United States Patent [19]

Yamauchi et al.

[11] Patent Number: 5,071,636

[45] Date of Patent: Dec. 10, 1991

[54] CHELATING COMPOUNDS AND THEIR USE

[75] Inventors: Hirohiko Yamauchi; Jun Takahashi; Sakae Okano; Shigemi Seri; Makoto Azuma, all of Chiba, Japan

[73] Assignee: Nihon Medi-Physics Co., Ltd., Hyogo, Japan

[21] Appl. No.: 291,278

[22] Filed: Dec. 28, 1988

[30] Foreign Application Priority Data

Dec. 29, 1987 [JP] Japan .................. 62-334036

[51] Int. Cl.$^5$ .............. A61K 43/00; A61K 49/02; C07C 323/03; C07F 11/00
[52] U.S. Cl. ............................. 424/1.1; 424/9; 534/14; 534/10; 544/63; 544/72; 544/78; 544/98; 544/224; 544/336; 544/357; 544/358; 546/1; 546/184; 546/186; 564/500
[58] Field of Search .................. 534/10, 15, 14; 424/1.1; 544/63, 72, 78, 98, 224, 336, 357, 358; 546/1, 184, 186; 564/500

[56] References Cited

U.S. PATENT DOCUMENTS

| | | | |
|---|---|---|---|
| 4,444,690 | 4/1984 | Fritzberg | 534/14 |
| 4,638,051 | 1/1987 | Burns et al. | 424/1.1 X |
| 4,849,511 | 7/1989 | Verbruggen | 534/14 |
| 4,925,650 | 5/1990 | Nosco | 424/1.1 |

FOREIGN PATENT DOCUMENTS

| | | |
|---|---|---|
| 163119 | 12/1985 | European Pat. Off. |
| 200211 | 11/1986 | European Pat. Off. |
| WO8600897 | 2/1986 | PCT Int'l Appl. |

OTHER PUBLICATIONS

Efange, S. M. N. et al., Journal of Nuclear Medicine, vol. 28, No. 6, pp. 1012-1019 (1987).
Efange, S. M. N. et al., Journal of Medicinal Chemistry, vol. 31, No. 5, pp. 1043-1047 (1988).
Kung, H. F. et al., The Journal of Nuclear Medicine, vol. 21, No. 2, pp. 147-152 (1980).
Kung, H. F. et al., The Journal of Nuclear Medicine, vol. 25, No. 3, pp. 326-332 (1984).
Loberg, M. D. et al., The Journal of Nuclear Medicine, vol. 21, No. 2, pp. 183-186 (1980).

*Primary Examiner*—Richard D. Lovering
*Assistant Examiner*—John M. Covert

[57] ABSTRACT

A polyaminedithiol compound of the formula:

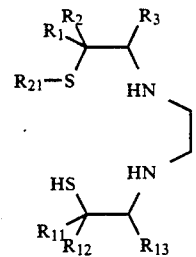

wherein $R_1$, $R_2$, $R_{11}$ and $R_{12}$ are each a lower alkyl group, $R_{21}$ is a hydrogen atom or a lower alkyl group, and $R_3$ and $R_{13}$ are each a hydrogen atom or a nitrogen-containing organic group, provided that at least one of $R_3$ and $R_{13}$ is a nitrogen-containing organic group, which is used for imaging of the regional cerebral blood flow.

10 Claims, No Drawings

CHELATING COMPOUNDS AND THEIR USE

The present invention relates to chelating compounds and their use. More particularly, it relates to chelating compounds which can be combined with a radioactive metal through a chelate bond to make complex compounds useful as radioactive diagnostic agents, and their use.

Imaging of regional cerebral blood flow by single photon emission computed tomography is performed to evaluate the blood flow and volume in the cerebral capillaries, whereby the diagnosis on the loci of the brain is made. In order to give an accurate diagnosis by imaging, it is required to use a diagnostic agent which can be administered intravenously and enter into the viable cells of the brain through the brain-blood barrier. While such diagnostic agent commonly carries a radioactive nuclide, the radioactivity emitted by the nuclide is required to stay at various parts of the brain in a sufficient amount and for a sufficient time without redistribution so as to make brain imaging possible.

For the purpose of providing a diagnostic agent which would meet the above requirements, studies were made on various compounds carrying radioactive nuclide such as I-131, Se-75, I-125, etc., but none of them could be used practically due to the improper half-life as well as the emission energy of gamma-rays.

Recently, there has been developed a physiologically active substance labeled with iodine-123 having a proper half-life and a relatively low emission energy of gamma-rays, i.e. N-isopropyl-2-methyl-p-iodo(I-123)-phenethylamine (hereinafter referred to as "I-123-IMP"). In fact, I-123-IMP is clinically used as an imaging agent for regional cerebral blood flow. However, I-123 is relatively expensive and not readily available. Because of this reason, further studies are in progress for making possible the use of any other radioactive nuclide which is less expensive and readily available. One of such radioactive nuclide is Tc-99m. Advantageously, Tc-99m emits an energy of gamma-rays suitable for the characteristics of a gamma camera and has a proper half-life and reduces exposure doses. Then, some 1,10-dithia-4,7-diaza-n-decane derivatives have been studied to label with Tc-99m, and it was noted that their Tc-99m complexes could pass through the brain-blood barrier [Kung H. F., et al: Journal of Nuclear Medicine, Vol. 25, pages 326-332 (1984)].

As a result of the extensive study, it has now been found that some polyaminedithiol compounds having a 1,10-dithia-4,7-diaza-n-decane structure could form chelate compounds with various radioactive metals through a firm chelate bonding. It has also been found that the chelate compounds thus formed were relatively stable and could be accumulated selectively at certain specific tissues and organs. Especially when Tc-99m is used as the radioactive metal, the resulting chelate compound is extremely stable and can be retained in the brain over a long period of time so that it is useful as an imaging agent for regional cerebral blood flow. The present invention is based on the above finding.

A basic object of the present invention is to provide a polyaminedithiol compound of the formula:

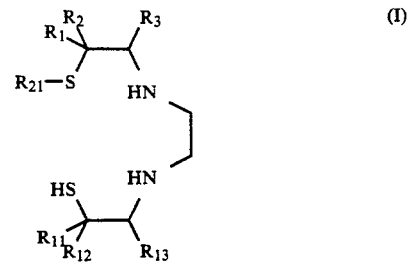

wherein $R_1$, $R_2$, $R_{11}$ and $R_{12}$ are each a lower alkyl group, $R_{21}$ is a hydrogen atom or a lower alkyl group, and $R_3$ and $R_{13}$ are each a hydrogen atom or a nitrogen-containing organic group, provided that at least one of $R_3$ and $R_{13}$ is a nitrogen-containing organic group, which can be coordinated with a radioactive metal to form a chelate compound useful as a radioactive diagnostic agent, particularly an imaging agent for regional cerebral blood flow.

The objective compounds of this invention include not only the polyaminedithiol compound (I) but also its salts. The term "lower" as hereinabove or hereinafter used is intended to mean a group having not more than 8 carbon atoms, particularly not more than 6 carbon atoms, more particularly not more than 3 carbon atoms, unless otherwise indicated. Preferred examples of "lower alkyl" are methyl, ethyl, etc.

The nitrogen-containing organic group may be, for instance, the one of the formula:

wherein A is a lower alkylene group, and $R_4$ and $R_5$ are each a hydrogen atom, a lower alkyl group, a cyclo($C_3$-$C_8$)alkyl group or a group of the formula:

(wherein A' is a lower alkylene group, and $R_6$ and $R_7$ are each a hydrogen atom, a lower alkyl group or a cyclo($C_3$-$C_8$)-alkyl group, or $R_6$ and $R_7$ are combined together with the adjacent nitrogen atom to form a substituted or unsubstituted 5 to 8-membered nitrogen-containing saturated heterocyclic group), or $R_4$ and $R_5$ are combined together with the adjacent nitrogen atom to form a substituted or unsubstituted 5 to 8-membered nitrogen-containing saturated heterocyclic group.

Examples of the nitrogen-containing organic group are amino(lower)alkyl, lower alkylamino(lower)alkyl, di(lower)alkylamino(lower)alkyl, piperidino(lower)alkyl, piperazino(lower)alkyl, pyrrolidino(lower)alkyl, 4-(lower)-alkylpiperazino(lower)alkyl, 4-(lower)alkyl-piperidino-(lower)alkyl, 4-phenyl(lower)alkyl-piperazino(lower)alkyl, 4-phenylpiperidino(lower)alkyl, morpholino(lower)alkyl, lower alkylamino(lower)alkylamino(lower)alkyl, di(lower)-alkylamino(lower)alkylamino(lower)alkyl, piperidino(lower)-alkylamino(lower)alkyl, piperazino(lower)alkylamino(lower)-alkyl, 4-(lower)alkylpiperazino(lower)alkylamino(lower)-alkyl, 4-phenyl(lower)alkyl-piperazino(lower)alkylamino(lower)alkyl, lower cycloalkylamino(lower)alkyl or morpholino(lower)alkylamino(lower)alkyl, etc., more specifically aminomethyl, propylaminomethyl, isopropylaminomethyl, butylaminomethyl, isobutylaminomethyl, pentylaminomethyl, 1-methylbutylaminomethyl, hexylaminomethyl, N,N-diethylaminomethyl, N-butyl-N-ethylaminomethyl, N,N-dipropylaminomethyl, piperidinomethyl, piperazinomethyl, pyrrolidinomethyl, 4-methylpiperazinomethyl, 4-methylpiperidinomethyl, 4-benzylpiperazinomethyl, 4-phenylpiperidinomethyl, morpholinomethyl, N,N-dimethylaminoethylaminomethyl, N,N-diethylaminoethylaminomethyl, piperidinoethylaminomethyl, piperazinoethylaminomethyl, 4-methylpiperazinoethylaminomethyl, 4-isopropylpiperazinoethylaminomethyl, 4-benzylpiperazinoethylaminomethyl, 2-morpholinoethylaminomethyl, cyclohexylaminomethyl, 3-morpholinopropylaminomethyl, etc.

The polyaminedithiol compound (I) can be prepared by various procedures, of which typical ones are set forth in Diagrams 1 to 4 as shown below. In Diagrams 1, 2 and 3, the procedures are shown by taking as an example the case wherein $R_1$, $R_2$, $R_{11}$ and $R_{12}$ are each methyl, and $R_{21}$ is hydrogen, and in Diagram 4, the procedure is shown by taking as an example the case wherein $R_1$, $R_2$, $R_{11}$ and $R_{12}$ are each methyl, and $R_{21}$ is butyl. It will be apparent to those skilled in the art that other polyaminedithiol compounds (I) are obtainable in the substantially same fashion as shown in the given Diagrams. Furthermore, the term "Pro" stands for a conventional protective group for a mercapto group (—SH) such as benzyl, and N and Ⓝ represent each a nitrogen-containing organic group, particularly a group of the formula: —N($R_4$)—$R_5$ (in which $R_4$ and $R_5$ are each as defined above).

Diagram 1

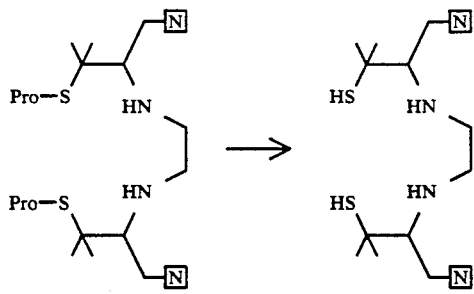

Diagram 2

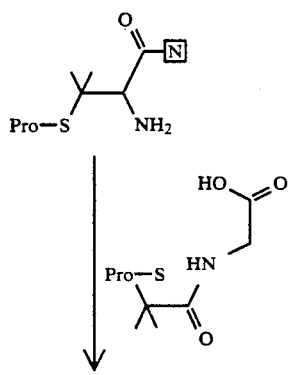

-continued

Diagram 1

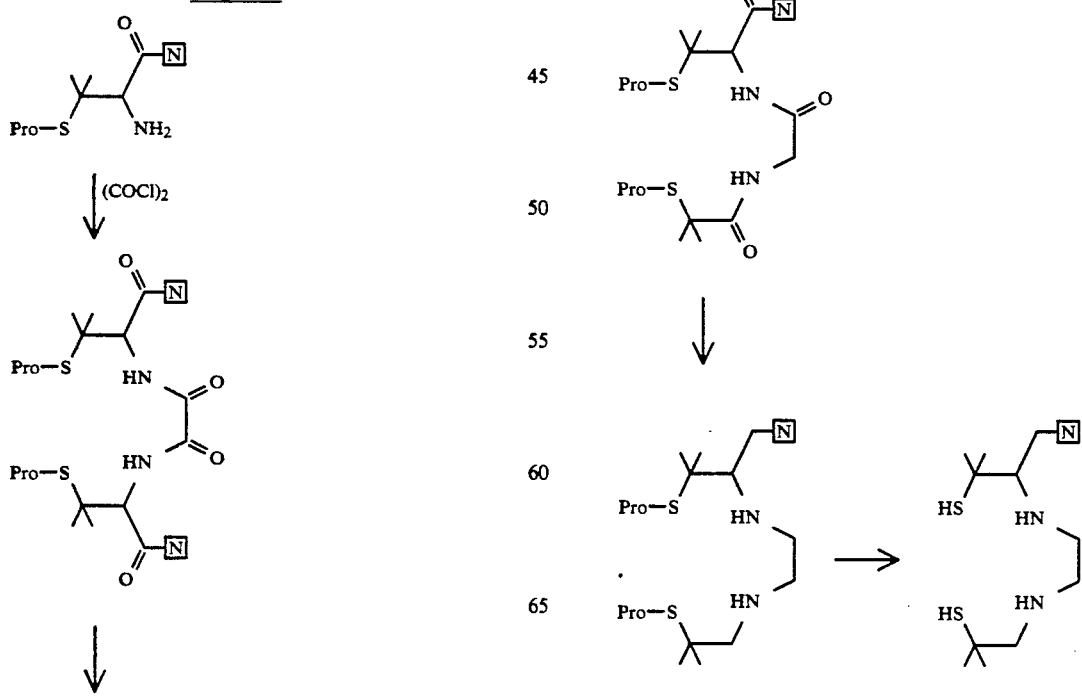

Diagram 3

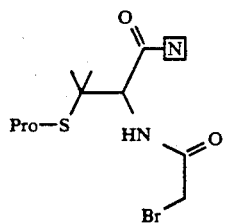

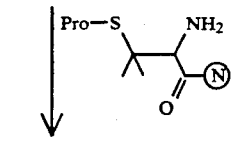

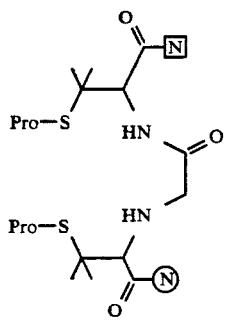

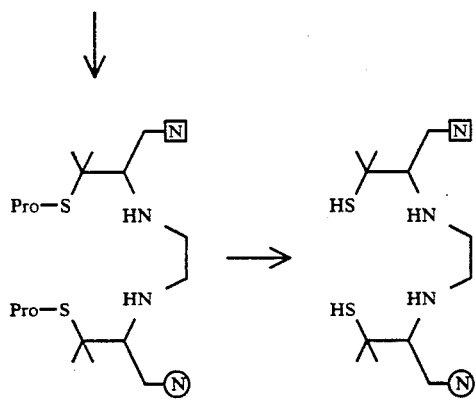

Diagram 4

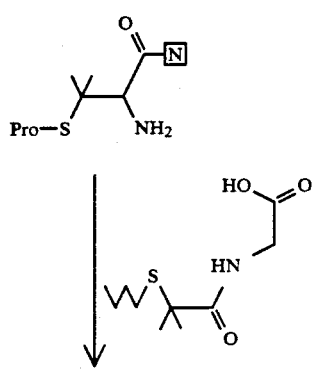

-continued
Diagram 4

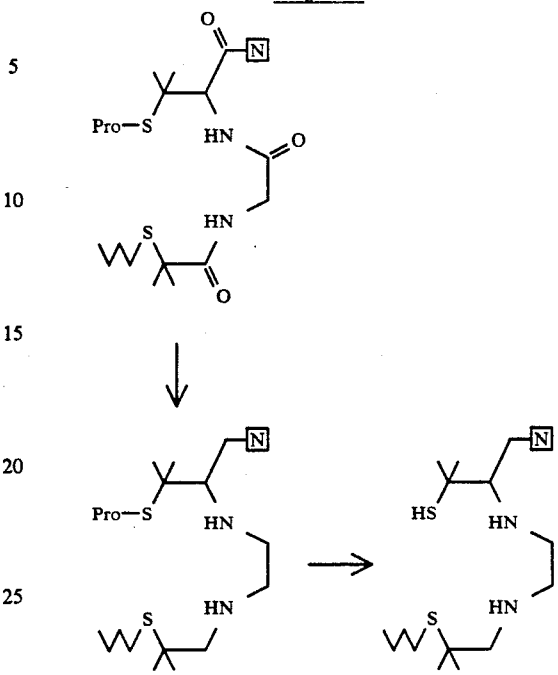

Diagram 1 shows a typical procedure for preparation of the polyaminedithiol compound (I) in a symmetrical form, which comprises three steps, i.e. condensation, reduction of the carbonyl group to a methylene group and elimination of the protective group. Diagram 2 shows a typical procedure for preparation of the polyaminedithiol compound (I) in an asymmetrical form (only one of $R_3$ and $R_{13}$ being a nitrogen-containing organic group), which comprises three steps, i.e. condensation, reduction of the carbonyl group to a methylene group and elimination of the protective group. Diagram 3 shows another typical procedure for preparation of the polyaminedithiol compound (I) in an asymmetrical form (both of $R_3$ and $R_{13}$ being nitrogen-containing organic groups), which comprises three steps, i.e. condensation, reduction of the carbonyl group to a methylene group and elimination of the protective group. Diagram 4 is a further typical procedure for preparation of the polyaminedithiol compound (I) in an asymmetrical form (only one of $R_3$ and $R_{13}$ being a nitrogen-containing organic group and $R_{21}$ being lower alkyl), which comprises three steps, i.e. condensation, reduction of the carbonyl group to a methylene group and elimination of the protective group. The chemical conversion at any step in the above procedures may be accomplished in a per se conventional manner.

The polyaminedithiol compound (I) according to the invention is per se useful as a carrier for radioactive metals. Namely, it can be firmly coordinated with a radioactive metal to form a chelate compound, which is extremely stable in vitro and in vivo and can be used as a radioactive diagnostic agent.

The polyaminedithiol compound (I) as a carrier for radioactive metal may be in the form of solution. Usually, it is converted into a powder form by lyophilization or distillation at low temperature under reduced pressure and stored in such powder form. On the use, the powder is dissolved in sterilized water, physiological saline solution, buffer, etc. The polyaminedithiol compound (I) in a solution or powder form may be incorporated with pharmaceutically acceptable solubilizing agents (e.g. organic solvents), pH regulating agents (e.g. acids, bases, buffers), stabilizers (e.g. ascorbic acid), preservatives (e.g. sodium benzoate), isotonizing agents (e.g. sodium chloride), etc., as well as reducing or oxidizing agents for adjustment of the atomic oxidation state of the radioactive metal.

As a radioactive metal, there may be used any metallic element having radioactivity, which has physical and chemical characteristics suitable for nuclear medical diagnosis and can be coordinated easily with the polyaminedithiol compound (I). Specific examples of the radioactive metallic element are gallium-67, gallium-68, thallium-201, indium-111, technetium-99m, zinc-62, copper-62, etc. They are normally employed in their salt forms, particularly their water-soluble salt forms.

Depending upon the chemical properties of the radioactive metal, there may be adopted two different labeling manners. When the radioactive metal is in an oxidation state which is not required to be reduced or oxidized for formation of a stable chelate compound, the polyaminedithiol compound (I) is reacted with the radioactive metal in an aqueous medium. This labeling manner may be applied to gallium-67, indium-111, etc. When the radioactive metal is in an oxidation state which is required to be reduced or oxidized for formation of a stable chelate compound, the polyaminedithiol compound (I) is reacted with the radioactive metal in an aqueous medium containing a reducing agent or an oxidizing agent. This labeling manner may be applied to technetium-99m. As a reducing agent, there may be usually employed a stannous salt, i.e. a salt of divalent tin ion (Sn ++). Specific examples are stannous halides (e.g. stannous chloride), stannous sulfate, stannous nitrate, stannous acetate, stannous citrate, etc. Examples of the oxidizing agent are hydrogen peroxide, etc.

When, for instance, the radioactive metal is technetium-99m, the polyaminedithiol compound (I) may be treated with technetium-99m in the form of pertechnetate in an aqueous medium containing a reducing agent such as a stannous salt. As to the order of the addition of the above reagents into the reaction mixture, any particular limitation does not exist. Usually, however, the mixing of the stannous salt with the pertechnetate in an aqueous medium in the first place should be avoided. The stannous salt may be used in such an amount as can reduce sufficiently the pertechnetate.

The radioactive diagnostic agent should have sufficient radioactivity and radioactivity concentration which can assure reliable diagnosis. For instance, in case of the radioactive metal being technetium-99m, it may be included usually in an amount of 0.1 to 50 mCi in about 0.5 to 5.0 ml at the time of administration. The amount of the polyaminedithiol compound (I) may be such as sufficient to form a stable chelate compound with the radioactive metal.

The thus formed chelate compound as a radioactive diagnostic agent is sufficiently stable, and therefore it may be immediately administered as such or stored until its use. When desired, the radioactive diagnostic agent may contain any additive such as pH controlling agents (e.g. acids, bases, buffers), stabilizers (e.g. ascorbic acid) or isotonizing agents (e.g. sodium chloride).

As explained above, the polyaminedithiol compound (I) of the invention can be coordinated with a radioactive metal to form a chelate compound and is therefore useful as a carrier for radioactive metal. The resulting chelate compound is highly stable in vitro and in vivo. It is highly lipophilic, has good permeability for a cell membrane and can pass through the brain-blood barrier easily. Also, it can be accumulated in the brain by a specific or nonspecific binding to a cerebral amine receptor. Due to these characteristics, the chelate compound is useful for nuclear medical diagnosis, particularly as an imaging agent for regional cerebral blood flow.

Practical and presently preferred embodiments of the invention are illustratively shown in the following Examples wherein part(s) and % are by weight unless otherwise indicated. Further, the abbreviations used herein have the following meanings:

Bzl : benzyl
Bzl(OMe): methoxybenzyl
Boc : t-butoxycarbonyl
FW : formula weight
IR : infrared spectroscopy
NMR : nuclear magnetic resonance
EP : electrophoresis

EXAMPLE 1

Preparation of N-(2-mercapto-2-methylpropyl)-N'-(1-isopropylaminomethyl-2-mercapto-2-methylpropyl)ethylene -diamine (hydrochloride (11c):

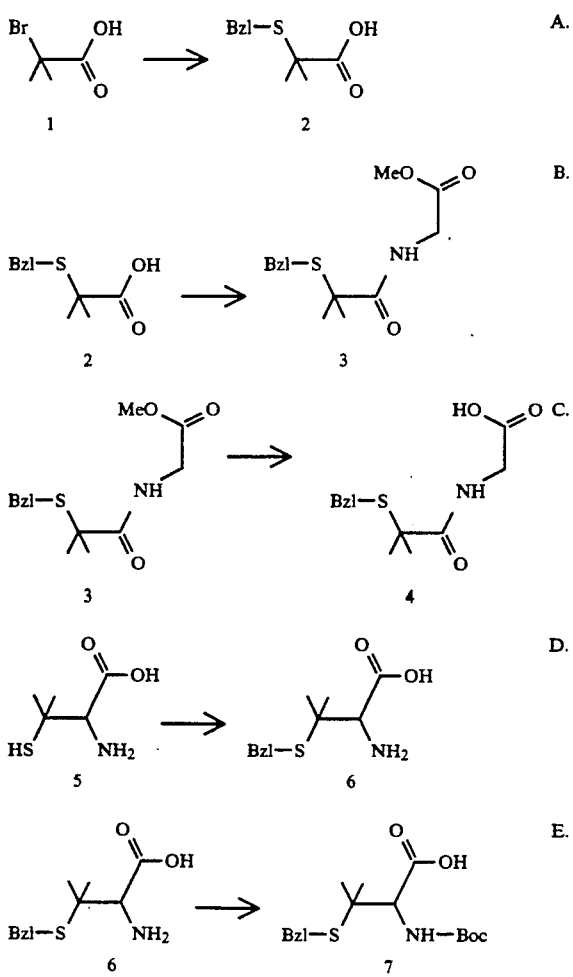

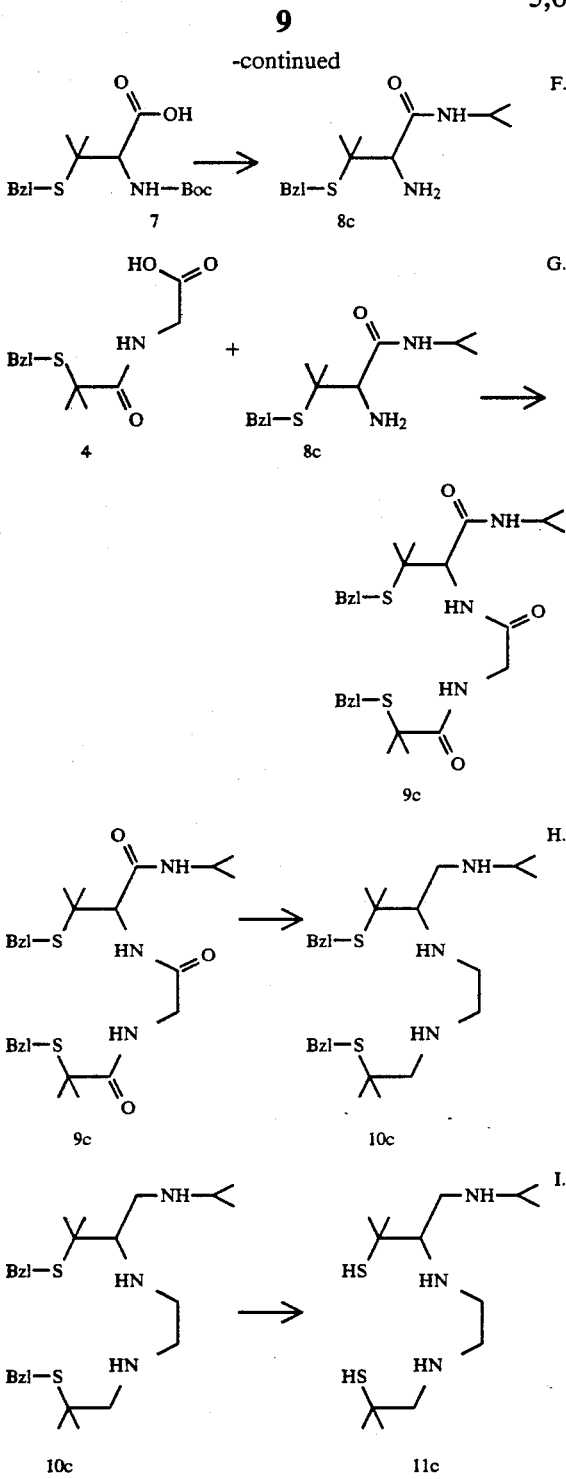

A. Benzylthioisobutyric acid (2)

Benzylmercaptan (415 ml; 3.5 mol) was added to isopropanol (800 ml), and under cooling, 5.3 N aqueous sodium hydroxide (1000 ml) and an isopropanol solution (800 ml) containing bromoisobutyric acid (1) (296 g; 1.77 mol) were dropwise added thereto. The resulting mixture was heated at 80° C. for 44 hours while stirring. The reaction mixture was combined with water (1000 ml) and washed with ether three times. The aqueous layer was adjusted to pH 2 with 4N hydrochloric acid, followed by extraction with ethyl acetate two times. The ethyl acetate layer was washed with water and a saturated aqueous solution of sodium chloride in order three times. The organic layers were combined together, dried over anhydrous sodium sulfate and concentrated. Ether (5 liters) was added to the residue, and dicyclohexylamine (353 ml) was dropwise added thereto under cooling. Precipitated crystals were collected by filtration and recrystallized from a mixture of methanol and ether to give benzylthioisobutyric acid (dicyclohexylamine salt) (2) (348.7 g; yield, 50%).

B. 2-Benzylthio-2-methylpropionylglycine methyl ester (3)

To a suspension of glycine methyl ester hydrochloride (108 g; 860 mmol) in chloroform (1000 ml), Compound (2) (337 g; 860 mmol) and dicyclohexylcarbodiimide (177.4 g; 860 mmol) were added while cooling at 0° C., and the resultant mixture was stirred at the same temperature for 1 hour and at room temperature overnight. After removal of insoluble materials, the reaction mixture was concentrated, and the residue was combined with ethyl acetate. The resulting mixture was washed with 5% aqueous sodium hydrogen carbonate, water, 5% aqueous citric acid and water in order three times and dried over anhydrous sodium sulfate, followed by concentration to give crude crystals. Recrystallization of said crude crystals from a mixture of ether and petroleum ether gave Compound (3) (137 g; yield, 66%).

C. 2-Benzylthio-2-methylpropionylglycine (4)

To a solution of Compound (3) (128.6 g; 458 mmol) in methanol (1400 ml), 1N aqueous sodium hydroxide (504 ml) was dropwise added while cooling at 0° C., and the resultant mixture was stirred at the same temperature for 1 hour and at room temperature for 3 hours, followed by concentration. The residue was diluted with a slight amount of water and washed with ether three times. The aqueous layer was collected, adjusted to pH 3 with 5% aqueous citric acid while cooling and extracted with ethyl acetate three times. The organic layer was washed with a saturated aqueous solution of sodium chloride three times, dried over anhydrous sodium sulfate and concentrated to give crude crystals. Recrystallization of said crude crystals from a mixture of ethyl acetate and petroleum ether gave Compound (4) (115.3 g; yield, 94%).

D. S-Benzyl-D-penicillamine (6)

D-Penicillamine (5)(140 9: 938 mmol) and sodium hydroxide (43 g; 938 mmol) were dissolved in a mixture of oxygen-free water (670 ml) and oxygen-free isopropanol (830 ml) at 0° C. To the resultant solution, benzyl bromide (208.6 g; 1219 mmol) was dropwise added, and the mixture was stirred at room temperature overnight. The reaction mixture was made neutral with 2N aqueous sodium hydroxide, stirred at −20° C. to precipitate crystals, which were collected by filtration to give Compound (6) (157.3 g; yield 70%).

E. S-Benzyl-Boc-D-penicillamine (7)

To a solution of Compound (6) (157.3 g; 657 mmol) in methanol (1200 ml), triethylamine (92 ml; 657 mmol) was dropwise added, and a solution of di-t-butyl dicarbonate (157.7 g; 723 mmol) in methanol (300 ml) was dropwise added thereto. The resultant mixture was stirred overnight and concentrated. The residue was combined with water (500 ml) and washed with ethyl acetate three times. The aqueous layers were collected, adjusted to pH 2 with 5% aqueous citric acid at 0° C. and extracted with ethyl acetate three times. The ethyl acetate layer was washed with a saturated aqueous sodium chloride solution three times, dried over anhydrous sodium sulfate and concentrated to give Compound (7) (243.3 g; yield, 100%).

F. S-Benzyl-D-penicillamineisopropylamide (8c)

To a solution of Compound (7) (33.9 g; 100 mmol) and isopropylamine (4.7 ml; 110 mmol) in tetrahydrofuran (180 ml), 1-hydroxybenzotriazole (20.3 g; 150 mmol) was added at 0° C. A solution of dicyclohexylcarbodiimide (22.7 g; 110 mmol) in tetrahydrofuran (60 ml) was dropwise added thereto, and the resultant mixture was stirred at 0° C. for 1 hour and at room temperature for 2.5 hours. After removal of insoluble materials by filtration, the filtrate was concentrated and combined with ethyl acetate (500 ml). The resulting mixture was washed with 10% citric acid, a saturated aqueous sodium chloride solution, a saturated aqueous sodium hydrogen carbonate solution and a saturated aqueous sodium chloride solution in order three times. The organic layer was collected, dried over anhydrous sodium sulfate and concentrated. To the residue, a 4N hydrogen chloride solution in dioxane (500 ml) was added, and the resultant mixture was stirred at 0° C. for 1 hour and at room temperature overnight, followed by concentration to give Compound (8c) (39.4 g; yield, 39.4%).

G. (2-Benzylthio-2-methylpropionylglycyl-S-benzyl-D-penicillamineisopropylamide (9c)

To a solution of Compound (8c) (39.4 g; 100 mmol) in tetrahydrofuran (200 ml), triethylamine (14 ml; 100 mmol) was added, and the resultant solution was cooled to 0° C. Compound (4) (26.7 g; 100 mmol) and 1-hydroxybenzotriazole (20.3 g; 150 mmol) were added thereto. After 5 minutes, a solution of dicyclohexylcarbodiimide (22.7 g; 110 mmol) in tetrahydrofuran (80 ml) was dropwise added thereto. The resultant solution was stirred at 0° C. for 1 hour and at room temperature overnight. After removal of insoluble materials by filtration, the filtrate was concentrated and combined with ethyl acetate (500 ml). The resulting mixture was washed with 10% citric acid, a saturated aqueous sodium chloride solution, a saturated aqueous sodium hydrogen carbonate solution and a saturated aqueous sodium chloride solution in order three times. The organic layer was collected, dried over anhydrous sodium sulfate, concentrated and purified by silica gel column chromatography with ether as an eluting solvent to give Compound (9c) (9.4 g; yield, 18%).

H. N-(2-Benzylthio-2-methylpropyl)-N'-[2-benzyl-thio-2-methyl-1-(isopropylamino)methylpropyl]ethylenediamine (10c)

Under nitrogen stream, a 1M diborane in tetrahydrofuran (600 ml) was cooled to 0° C., and a tetrahydrofuran solution (70 ml) containing Compound (9c) (8.3 g; 15.7 mmol) was dropwise added thereto. The resultant mixture was gradually heated and refluxed for 24 hours, followed by cooling. 6N Hydrochloric acid (62.8 ml) was dropwise added to the reaction mixture, which was stirred at room temperature overnight. After removal of insoluble materials by filtration, the reaction mixture was concentrated. The residue was combined with water (100 ml) and ether (100 ml) and stirred. The aqueous layer was collected and washed with ether two times, followed by cooling. The aqueous layer was adjusted to pH 11 with potassium carbonate and extracted with chloroform three times. The extract was washed with a saturated aqueous sodium chloride solution twice, dried over anhydrous sodium sulfate and concentrated. The residue was combined with a 4N hydrogen chloride solution in dioxane (23.6 ml) under cooling, followed by concentration. The residue was purified by silica gel column chromatography with a mixture of chloroform and methanol (10 : 1) as an eluting solvent to give Compound (10c) (HCl salt) (4.1 g; yield, 43%).

I. N-(2-Mercapto-2-methylpropyl)-N'-[1-(isopropylamino)methyl-2-mercapto-2-methylpropyl]ethylenediamine (11c)

Compound (10c) (HCl salt) (4.1 g; 6.86 mmol) was dissolved in 10% potassium carbonate, and the resultant solution was adjusted to pH 11 and extracted with chloroform three times, followed by washing with a saturated aqueous sodium chloride solution. The organic layer was dried over anhydrous sodium sulfate, concentrated and combined with tetrahydrofuran (50 ml). Under nitrogen stream, the tetrahydrofuran solution was added to liquid ammonia (1 liter), and metallic lithium (1.7 g; 247 mmol) was added thereto. The resultant mixture was confirmed to be colored in blue and stirred for 6 hours. Ammonium chloride (14.5 g; 272 mmol) was added thereto, whereby the reaction was stopped. After 10 minutes, ammonia was spontaneously evaporated therefrom. Methanol was added to the residue, which was concentrated and mixed with water (50 ml) and 2N hydrochloric acid (22.6 ml). After removal of insoluble materials, the reaction mixture was washed with ether two times. The aqueous layer was adjusted to pH 11 with potassium carbonate and extracted with chloroform three times. The extract was washed with a saturated aqueous sodium chloride solution two times, dried over anhydrous sodium sulfate and concentrated. A 4N hydrogen chloride solution in dioxane (11.3 ml) was added to the residue at 0° C., and the resultant mixture was warmed to room temperature, concentrated and combined with methanol (10 ml), followed by addition of cold ether (1 liter) for precipitation under cooling. Upon reprecipitation, there was obtained Compound (11c) (HCl salt) (1.6 g; yield, 56%).

Compound (11c) (HCl salt) (20 mg) was adjusted to pH 11 with addition of 10% aqueous potassium carbonate and extracted with chloroform three times. The organic layer was washed with a saturated aqueous sodium chloride solution, dried over anhydrous sodium sulfate and concentrated. The residue was subjected to IR and NMR analysis, whereas Compound (11c) (HCl salt) was subjected to elementary analysis. The results are shown in Tables 1 and 2.

TABLE 1

| | Compound (11c) |
|---|---|
| IR (NaCl): | $CH_3$ (2960 $cm^{-1}$), $CH_2$ (1460, 2925 $cm^{-1}$), CH (1340, 2890 $cm^{-1}$), $(CH_3)_2CH$ (1170, 1380 $cm^{-1}$), NH (3300 $cm^{-1}$), SH (2540 $cm^{-1}$). |
| NMR (CDCl$_3$, TMS): | $(CH_3)_2CH$ (1.08 ppm, d), $(CH_3)_2C=$ (1.41 ppm, s), NH (1.81 ppm, s), $(CH_3)_2CH$ (3.76 ppm, m), CH, $CH_2$, |

TABLE 1-continued

| Compound (11c) |
|---|
| SH (2.43–3.20 ppm). |

TABLE 2

| Compound (11c) (HCl salt) $C_{14}H_{33}N_3S_2.3HCl.H_2O$ (FW = 434.96) | | |
|---|---|---|
| | Calcd. (%): | Found (%): |
| C | 38.66 | 38.51 |
| H | 8.81 | 8.90 |
| N | 9.66 | 9.72 |
| S | 14.74 | 14.58 |
| Cl | 24.45 | 24.56 |

EXAMPLE 2

Preparation of polyaminedithiol compounds (Part I)

In the same manner as in Example 1 F but replacing isopropylamine by other amines, there were prepared 16 kinds of polyaminedithiol compounds (11a, 11b, 11d, 11g, 11i, 11k, 11l, 11m, 11n, 11o, 11h, 11p, 11r, 11w, 11x and 11zc) as shown in Table 3 where the names of the starting amines and the yields (%) in each step from the starting amines to the produced polyaminedithiol compounds are given. The names of the produced polyaminedithiol compounds and their chemical structures and physical properties such as IR and NMR are given in Tables 4-1 to 4-16, and the data of their elementary analysis are given in Tables 5-1 to 5-16.

TABLE 3

| Amine | Product | Yield (%) |
|---|---|---|
| 1-Aminoethylpiperazine | 8a* | 100 |
| | 9a* | 50 |
| | 10a* | 39 |
| | 11a | 5 |
| 1-Aminoethylpiperidine | 8b | 100 |
| | 9b | 52 |
| | 10b | 59 |
| | 11b | 87 |
| n-Amylamine | 8d | 100 |
| | 9d | 47 |
| | 10d | 68 |
| | 11d | 54 |
| Piperidine | 8g | 94 |
| | 9g | 57 |
| | 10g | 76 |
| | 11g | 15 |
| 1-Methylpiperazine | 8i | 100 |
| | 9i | 69 |
| | 10i | 55 |
| | 11i | 75 |
| Morpholine | 8k | 100 |
| | 9k | 48 |
| | 10k | 92 |
| | 11k | 26 |
| 2-Aminopentane | 8l | 97 |
| | 9l | 64 |
| | 10l | 46 |
| | 11l | 68 |
| n-Hexylamine | 8m | 96 |
| | 9m | 46 |
| | 10m | 86 |
| | 11m | 67 |
| Ethylbutylamine | 8n | 97 |
| | 9n | 48 |
| | 10n | 68 |
| | 11n | 36 |
| Dipropylamine | 8o | 100 |
| | 9o | 58 |
| | 10o | 46 |
| | 11o | 84 |
| Piperazine | 8h* | 100 |
| | 9h* | 54 |
| | 10h* | 50 |
| | 11h | 54 |
| 4-Methylpiperidine | 8p | 100 |
| | 9p | 47 |
| | 10p | 72 |
| | 11p | 30 |
| Pyrrolidine | 8r | 100 |
| | 9r | 58 |
| | 10r | 63 |
| | 11r | 7 |
| 4-Benzylpiperazine | 8w | 70 |
| | 9w | 36 |
| | 10w | 58 |
| | 11w | 27 |
| 4-Phenylpiperidine | 8x | 100 |
| | 9x | 47 |
| | 10x | 49 |
| | 11x | 77 |
| Cyclohexylamine | 8zc | 100 |
| | 9zc | 52 |
| | 10zc | 62 |
| | 11zc | 40 |

Note:
*These compounds were tosylated at the 4-position.

TABLE 4-1

N-(2-Mercapto-2-methylpropyl)-N'-[2-mercapto-2-methyl-1-(2-piperazino-ethyl)aminomethylpropyl]ethylenediamine (11a)

Structure:

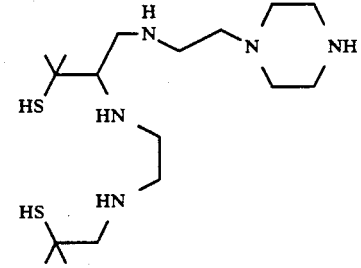

IR (NaCl): $CH_3$ (2950 cm$^{-1}$), $CH_2$ (1460, 2930 cm$^{-1}$), CH (1330 cm$^{-1}$), $(CH_3)C=$ (1210 cm$^{-1}$), NH (3300 cm$^{-1}$), SH (2540 cm$^{-1}$).

NMR (CDCl$_3$, TMS): (C$\underline{H}_3$)$_2$C= (1.31 ppm, s, 1.39 ppm, s), N$\underline{H}$ (1.86 ppm, s), C$\underline{H}$, C$\underline{H}_2$, S$\underline{H}$ (2.43–3.30 ppm).

TABLE 4-2

N-(2-Mercapto-2-methylpropyl)-N'-[2-mercapto-2-methyl-1-(2-piperidino-ethylamino)methylpropyl]ethylene-diamine (11b)

Structure:

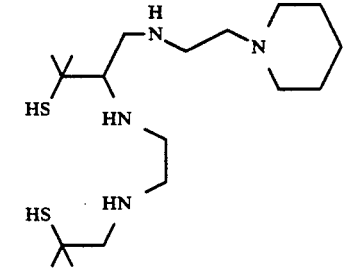

IR (NaCl): $CH_3$ (2950 cm$^{-1}$), $CH_2$ (1460, 2925 cm$^{-1}$), $(CH_3)_2CH$ (1380 cm$^{-1}$), NH (3300 cm$^{-1}$), CH (1340 cm$^{-1}$).

NMR (CDCl$_3$, TMS): (C$\underline{H}_3$)$_2$C= (1.38 ppm, s), N⌒CH$_2$⌒ (1.46 ppm, b), N$\underline{H}$ (1.93 ppm, s), C$\underline{H}$, C$\underline{H}_2$, S$\underline{H}$ (2.15–3.10 ppm).

TABLE 4-3

N-(2-Mercapto-2-methylpropyl)-N'-(1-n-amylaminomethyl-2-mercapto-2-methylpropyl)ethylenediamine (11d)

Structure:

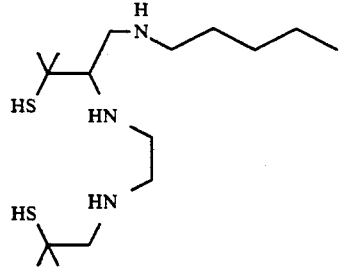

IR (NaCl): CH₃ (2960 cm⁻¹), CH₂ (1460, 2925 cm⁻¹), CH (1335 cm⁻¹), (CH₃)C= (1380 cm⁻¹), NH (3300 cm⁻¹), SH (2550 cm⁻¹).
NMR (CDCl₃, TMS): NH(CH₂)₄C$\underline{H}$₃ (1.96 ppm), (C$\underline{H}$₃)C= (1.40 ppm, s), NH(CH₂)₂C$\underline{H}$₂C$\underline{H}$₂CH₃ (1.35 ppm, b), N$\underline{H}$ (1.95 ppm, s), C$\underline{H}$, C$\underline{H}$₂, S$\underline{H}$ (2.30–3.30 ppm).

TABLE 4-4

N-(2-Mercapto-2-methylpropyl)-N'-(2-mercapto-2-methyl-1-piperidino-methylpropyl)ethylenediamine (11g)

Structure:

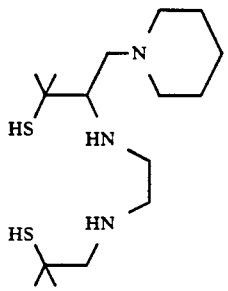

IR (NaCl): CH₃ (2950 cm⁻¹), CH₂ (1460 cm⁻¹), CH (1340 cm⁻¹), (CH₃)C= (1380 cm⁻¹), NH (3300 cm⁻¹), SH (2550 cm⁻¹).
NMR (CDCl₃, TMS): (C$\underline{H}$₃)₂C= (1.36 ppm, s, 1.41 ppm, s), N⟨CH₂⟩ (1.50 ppm, b), N$\underline{H}$ (1.81 ppm, s), C$\underline{H}$, C$\underline{H}$₂, S$\underline{H}$ (2.10–3.00 ppm).

TABLE 4-5

N-(2-Mercapto-2-methylpropyl)-N'-[2-mercapto-2-methyl-1-(4-methyl-piperazino)methylpropyl]ethylene-diamine (11i)

Structure:

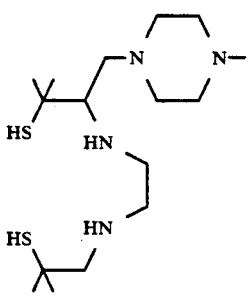

IR (NaCl): CH₃ (2950 cm⁻¹), CH₂ (1460 cm⁻¹), CH (1340, 2890 cm⁻¹), (CH₃)₂C= (1380 cm⁻¹), NH (3300 cm⁻¹), SH (2550 cm⁻¹).
NMR (CDCl₃, TMS): (C$\underline{H}$₃)C= (1.37 ppm, s, 1.42 ppm, s), N$\underline{H}$ (1.96 ppm, s), N—C$\underline{H}$₃, C$\underline{H}$, C$\underline{H}$₂, S$\underline{H}$ (2.18–3.20 ppm).

TABLE 4-6

N-(2-Mercapto-2-methylpropyl)-N'-(2-mercapto-2-methyl-1-morpholino-methylpropyl)ethylenediamine (11k)

Structure:

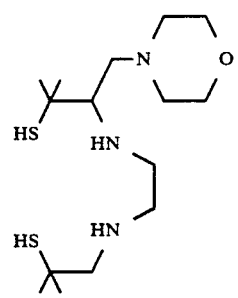

IR (NaCl): CH₃ (2965 cm⁻¹), CH₂ (1460, 2925 cm⁻¹), CH (1340, 2899 cm⁻¹), (CH₃)₂C= (1385 cm⁻¹), NH (3300 cm⁻¹), SH (2540 cm⁻¹), N(CH₂—CH₂)₂O (1120 cm⁻¹).

NMR (CDCl₃, TMS): (C$\underline{H}$₃)C= (1.37 ppm, s, 1.41 ppm, s), N$\underline{H}$ (2.05 ppm, s), N(CH₂—CH₂)₂O (3.72 ppm, t), C$\underline{H}$, C$\underline{H}$₂, S$\underline{H}$ (2.30–3.20 ppm).

TABLE 4-7

N-(2-Mercapto-2-methylpropyl)-N'-[1-(1-methylbutylamino)-methyl-2-mercapto-2-methylpropyl]ethylene-diamine (11l)

Structure:

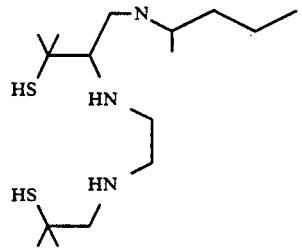

IR (NaCl): CH₃ (2980 cm⁻¹), CH₂ (1465, 2950 cm⁻¹), CH 1340, 2890 cm⁻¹), (CH₃)₂C= (1380 cm⁻¹), NH (3300 cm⁻¹), SH (2550 cm⁻¹).
NMR (CDCl₃, TMS): NHCH(CH₃)CH₂CH₂C$\underline{H}$₃ (1.91 ppm, t), NHCH(C$\underline{H}$₃)CH₂CH₂CH₃ (1.06 ppm, d), NHCH(CH₃)C$\underline{H}$₂C$\underline{H}$₂CH₃ (1.35 ppm, m), (C$\underline{H}$₃)₂C= (1.39 ppm, s), N$\underline{H}$ (1.80 ppm, s), C$\underline{H}$₂, C$\underline{H}$, S$\underline{H}$ (2.15–3.20 ppm).

TABLE 4-8

N-(2-Mercapto-2-methylpropyl)-N'-(1-n-hexylaminomethyl-2-mercapto-2-methylpropyl)ethylenediamine (11m)

Structure:

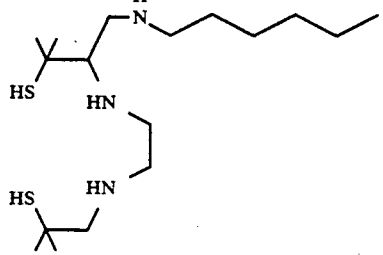

IR (NaCl): CH₃ (2980 cm⁻¹), CH₂ (1475, 2950 cm⁻¹),

TABLE 4-8-continued (CH$_3$)$_2$C= (1380 cm$^{-1}$), NH (3325 cm$^{-1}$), SH (2550 cm$^{-1}$).
NMR (CDCl$_3$, TMS): NH(CH$_2$)$_5$CH$_3$ (0.90 ppm, t), (CH$_3$)$_2$C=, NH(CH$_2$)$_2$(CH$_2$)$_3$CH$_3$ (1.40 ppm, b), NH (1.96 ppm, s), CH, CH$_2$, SH (2.25–3.10 ppm).

TABLE 4-9

N-(2-Mercapto-2-methylpropyl)-N'-[1-(N-butyl-N-ethylamino)-methyl-2-mercapto-2-methylpropyl]ethylenediamine (11n)

Structure:

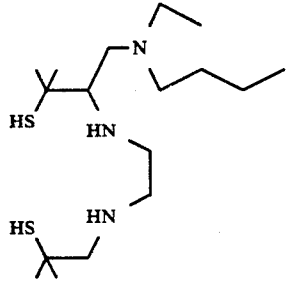

IR (NaCl): CH$_3$ (2980 cm$^{-1}$), CH$_2$ (1465, 2950 cm$^{-1}$), CH (2890 cm$^{-1}$), (CH$_3$)$_2$C= (1380 cm$^{-1}$), NH (3300 cm$^{-1}$).
NMR (CDCl$_3$, TMS): CH$_3$CH$_2$N(CH$_2$)$_3$CH$_3$ (0.80–1.18 ppm), (CH$_3$)C=, NCH$_2$CH$_2$CH$_3$ (1.20–1.70 ppm), NH (1.88 ppm, s), CH, SH, CH$_2$ (2.20–3.15 ppm).

TABLE 4-10

N-(2-Mercapto-2-methylpropyl)-N'-[1-(N,N-dipropylamino)methyl-2-mercapto-2-methylpropyl]ethylenediamine (11o)

Structure:

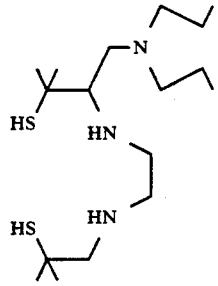

IR (NaCl): CH$_3$ (2960 cm$^{-1}$), CH$_2$ (1460, 2945 cm$^{-1}$), (CH$_3$)$_2$C= (1380 cm$^{-1}$), NH (3300 cm$^{-1}$), SH (2550 cm$^{-1}$).
NMR (CDCl$_3$, TMS): N(CH$_2$CH$_2$CH$_3$)$_2$ (0.90 ppm, t), N(CH$_2$CH$_2$CH$_3$)$_2$, (CH$_3$)$_2$C= (1.15–1.80 ppm), NH (1.90 ppm, s), CH, CH$_2$, SH (2.20–3.30 ppm).

TABLE 4-11

N-(2-Mercapto-2-methylpropyl)-N'-(2-mercapto-2-methyl-1-piperazinomethylpropyl)ethylenediamine (11h)

Structure:

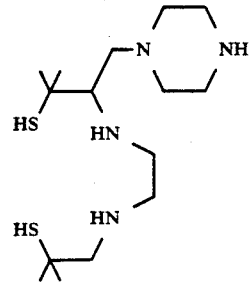

TABLE 4-11-continued

N-(2-Mercapto-2-methylpropyl)-N'-(2-mercapto-2-methyl-1-piperazinomethylpropyl)ethylenediamine (11h)

IR (NaCl): CH$_3$ (2960 cm$^{-1}$), CH$_2$ (1470, 2950 cm$^{-1}$), CH (1340, 2850 cm$^{-1}$), (CH$_3$)$_2$C= (1380 cm$^{-1}$), NH (3325 cm$^{-1}$), SH (2550 cm$^{-1}$).
NMR (CDCl$_3$, TMS): (CH$_3$)C= (1.32 ppm, s, 1.38 ppm, s), NH (1.81 ppm, s), CH, CH$_2$, SH (2.27–2.95 ppm).

TABLE 4-12

N-(2-Mercapto-2-methylpropyl)-N'-[2-mercapto-2-methyl-1-(4-methylpiperidino)methylpropyl]ethylenediamine (11p)

Structure:

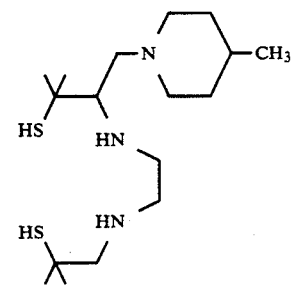

IR (NaCl): CH$_3$ (2960 cm$^{-1}$), CH$_2$ (1470, 2950 cm$^{-1}$), CH (1340, 2850 cm$^{-1}$), (CH$_3$)$_2$C= (1380 cm$^{-1}$), NH (3325 cm$^{-1}$), SH (2550 cm$^{-1}$).
NMR (CDCl$_3$, TMS): (CH$_3$)C= (1.32 ppm, s, 1.38 ppm, s), NH (1.81 ppm, s), CH, CH$_2$, SH (2.27–4.10 ppm), (CH$_3$)$_2$CCHCH$_3$ (0.6 ppm, d).

TABLE 4-13

N-(2-Mercapto-2-methylpropyl)-N'-(2-mercapto-2-methyl-1-pyrrolidinomethylpropyl)ethylenediamine (11r)

Structure:

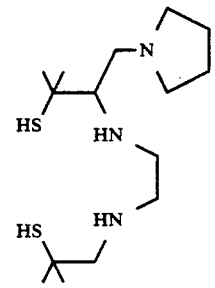

IR (NaCl): CH$_3$ (2900 cm$^{-1}$), CH$_2$ (1440 cm$^{-1}$), CH (1345, 2890 cm$^{-1}$), (CH$_3$)$_2$C= (1370 cm$^{-1}$), NH (3280 cm$^{-1}$), SH (2550 cm$^{-1}$).
NMR (CDCl$_3$, TMS): (CH$_3$)C= (1.38 ppm, s), NH (2.10 ppm, s), CH, CH$_2$, SH (2.22–3.20 ppm).

TABLE 4-14

N-(2-Mercapto-2-methylpropyl)-N'-[1-(4-benzylpiperazino)methyl-2-mercapto-2-methylpropyl]ethylenediamine (11w)

Structure:

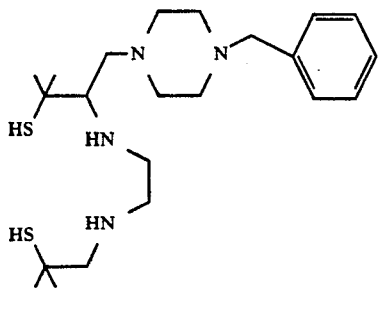

IR (NaCl): CH$_3$ (2930 cm$^{-1}$), CH$_2$ (1455, 2890 cm$^{-1}$), CH (1340, 2820 cm$^{-1}$), (CH$_3$)$_2$C= (1370 cm$^{-1}$), NH (3300 cm$^{-1}$), SH (2550 cm$^{-1}$),  (3050 cm$^{-1}$).

NMR (CDCl$_3$, TMS): (C$\underline{H}_3$)C= (1.25 ppm, s, 1.38 ppm, s), N$\underline{H}$ (1.87 ppm, s), —C$\underline{H}_2$ (3.45 ppm, s), — (7.23 ppm, s), C$\underline{H}$, C$\underline{H}_2$, S$\underline{H}$ (2.27–2.95 ppm).

TABLE 4-15

N-(2-Mercapto-2-methylpropyl)-N'-[2-mercapto-2-methyl-1-(4-phenylpiperidino)methylpropyl]ethylenediamine (11x)

Structure:

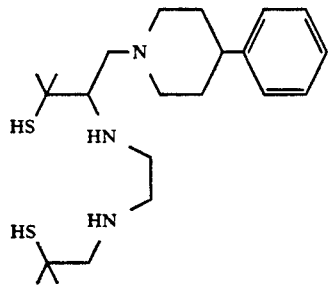

IR (NaCl): CH$_3$ (2980 cm$^{-1}$), CH$_2$ (1460, 2890 cm$^{-1}$), CH (1340, 2750 cm$^{-1}$), (CH$_3$)$_2$C= (1370 cm$^{-1}$), NH (3300 cm$^{-1}$), SH (2550 cm$^{-1}$),  (3030 cm$^{-1}$).

NMR (CDCl$_3$, TMS): (C$\underline{H}_3$)C= (1.30 ppm, s, 1.35 ppm, s), N$\underline{H}$ (2.05 ppm, s), —C$\underline{H}_2$ (3.45 ppm, s), — (7.25 ppm, s), C$\underline{H}$, C$\underline{H}_2$, S$\underline{H}$ (2.35–3.00 ppm).

TABLE 4-16

N-(2-Mercapto-2-methylpropyl)-N'-(1-cyclohexylaminomethyl-2-mercapto-2-methylpropyl)ethylenediamine (11zc)

Structure:

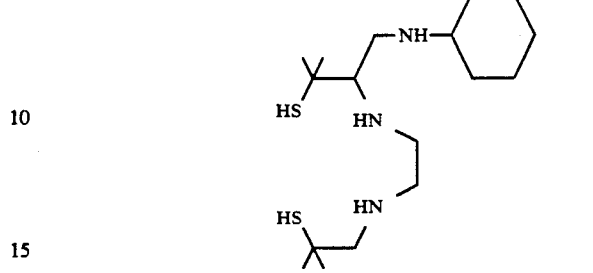

IR (NaCl): CH$_3$ (2950 cm$^{-1}$), CH$_2$ (1460 cm$^{-1}$), CH (1340 cm$^{-1}$), (CH$_3$)$_2$C= (1380 cm$^{-1}$), NH (3300 cm$^{-1}$), SH (2550 cm$^{-1}$).

NMR (CDCl$_3$, TMS): (C$\underline{H}_3$)C= (1.32 ppm, s, 1.38 ppm, s), N$\underline{H}$ (1.87 ppm, s), C$\underline{H}$, C$\underline{H}_2$, S$\underline{H}$ (2.22–2.93 ppm).

TABLE 5-1

Compound (11a) (HCl salt)
C$_{17}$H$_{39}$N$_5$S$_2$.5HCl.½H$_2$O (FW = 568.96)

| | Calcd. (%): | Found (%): |
|---|---|---|
| C | 35.89 | 35.85 |
| H | 7.97 | 8.03 |
| N | 12.31 | 12.21 |
| S | 11.27 | 11.25 |
| Cl | 31.16 | 31.05 |

TABLE 5-2

Compound (11b) (HCl salt)
C$_{18}$H$_{40}$N$_4$S$_2$.4HCl.2H$_2$O (FW = 558.54)

| | Calcd. (%): | Found (%): |
|---|---|---|
| C | 38.71 | 38.71 |
| H | 8.66 | 8.65 |
| N | 10.03 | 10.18 |
| S | 11.48 | 11.47 |
| Cl | 25.39 | 25.30 |

TABLE 5-3

Compound (11d) (HCl salt)
C$_{17}$H$_{39}$N$_5$S$_2$.5HCl.3/2H$_2$O (FW = 568.96)

| | Calcd. (%): | Found (%): |
|---|---|---|
| C | 40.71 | 40.65 |
| H | 9.18 | 9.17 |
| N | 8.90 | 8.93 |
| S | 13.58 | 13.42 |
| Cl | 22.53 | 22.73 |

TABLE 5-4

Compound (11g) (HCl salt)
C$_{16}$H$_{35}$N$_3$S$_2$.3HCl.H$_2$O (FW = 460.99)

| | Calcd. (%): | Found (%): |
|---|---|---|
| C | 41.69 | 41.55 |
| H | 8.75 | 8.87 |
| N | 9.12 | 9.07 |
| S | 13.91 | 13.80 |
| Cl | 23.07 | 23.11 |

TABLE 5-5

Compound (11i) (HCl salt)
$C_{16}H_{36}N_4S_2 \cdot 4HCl \cdot 2H_2O$ (FW = 530.48)

| | Calcd. (%): | Found (%): |
|---|---|---|
| C | 36.23 | 36.19 |
| H | 8.36 | 8.45 |
| N | 10.56 | 10.49 |
| S | 12.09 | 12.09 |
| Cl | 26.73 | 26.67 |

TABLE 5-6

Compound (11k) (HCl salt)
$C_{15}H_{33}N_3OS_2 \cdot 3HCl \cdot H_2O$ (FW = 462.96)

| | Calcd. (%): | Found (%): |
|---|---|---|
| C | 38.92 | 38.97 |
| H | 8.27 | 8.39 |
| N | 9.08 | 9.03 |
| S | 13.85 | 13.77 |
| Cl | 22.97 | 22.85 |

TABLE 5-7

Compound (11l) (HCl salt)
$C_{16}H_{37}N_3S_2 \cdot 3HCl \cdot 3/2H_2O$ (FW = 472.02)

| | Calcd. (%): | Found (%): |
|---|---|---|
| C | 40.71 | 40.91 |
| H | 9.18 | 9.07 |
| N | 8.90 | 8.83 |
| S | 13.58 | 13.63 |
| Cl | 22.53 | 22.45 |

TABLE 5-8

Compound (11m) (HCl salt)
$C_{17}H_{39}N_3S_2 \cdot 3HCl \cdot H_2O$ (FW = 477.04)

| | Calcd. (%): | Found (%): |
|---|---|---|
| C | 42.80 | 42.94 |
| H | 9.30 | 9.18 |
| N | 8.81 | 8.77 |
| S | 13.44 | 13.51 |
| Cl | 22.30 | 22.27 |

TABLE 5-9

Compound (11n) (HCl salt)
$C_{17}H_{39}N_3S_2 \cdot 3HCl \cdot H_2O$ (FW = 477.04)

| | Calcd. (%): | Found (%): |
|---|---|---|
| C | 42.80 | 42.75 |
| H | 8.24 | 7.99 |
| N | 8.81 | 9.13 |
| S | 13.44 | 13.71 |
| Cl | 22.30 | 22.57 |

TABLE 5-10

Compound (11o) (HCl salt)
$C_{17}H_{39}N_3S_2 \cdot 3HCl \cdot 3/2H_2O$ (FW = 486.04)

| | Calcd. (%): | Found (%): |
|---|---|---|
| C | 42.01 | 42.06 |
| H | 9.33 | 9.41 |
| N | 8.65 | 8.49 |
| S | 13.19 | 13.15 |
| Cl | 21.88 | 21.92 |

TABLE 5-11

Compound (11h) (HCl salt)
$C_{15}H_{34}N_4S_2 \cdot 4HCl \cdot H_2O$ (FW = 498.44)

| | Calcd. (%): | Found (%): |
|---|---|---|
| C | 36.15 | 36.15 |
| H | 8.09 | 8.14 |

TABLE 5-11-continued

Compound (11h) (HCl salt)
$C_{15}H_{34}N_4S_2 \cdot 4HCl \cdot H_2O$ (FW = 498.44)

| | Calcd. (%): | Found (%): |
|---|---|---|
| N | 11.24 | 11.15 |
| S | 12.86 | 12.83 |
| Cl | 28.45 | 28.37 |

TABLE 5-12

Compound (11p) (HCl salt)
$C_{17}H_{37}N_3S_2 \cdot 3HCl \cdot 2H_2O$ (FW = 493.03)

| | Calcd. (%): | Found (%): |
|---|---|---|
| C | 41.41 | 41.39 |
| H | 9.00 | 9.02 |
| N | 8.52 | 8.48 |
| S | 13.01 | 12.95 |
| Cl | 21.57 | 21.60 |

TABLE 5-13

Compound (11r) (HCl salt)
$C_{15}H_{34}N_3S_2 \cdot 3HCl \cdot 2H_2O$ (FW = 464.98)

| | Calcd. (%): | Found (%): |
|---|---|---|
| C | 38.75 | 38.72 |
| H | 8.67 | 8.79 |
| N | 9.02 | 9.11 |
| S | 13.79 | 13.64 |
| Cl | 22.87 | 22.77 |

TABLE 5-14

Compound (11w) (HCl salt)
$C_{22}H_{40}N_4S_2 \cdot 4HCl \cdot H_2O$ (FW = 588.57)

| | Calcd. (%): | Found (%): |
|---|---|---|
| C | 44.90 | 44.89 |
| H | 7.88 | 7.95 |
| N | 9.52 | 9.80 |
| S | 10.89 | 10.64 |
| Cl | 24.09 | 23.95 |

TABLE 5-15

Compound (11x) (HCl salt)
$C_{22}H_{39}N_3S_2 \cdot 3HCl \cdot 3/2H_2O$ (FW = 546.10)

| | Calcd. (%): | Found (%): |
|---|---|---|
| C | 48.39 | 48.28 |
| H | 8.31 | 8.60 |
| N | 7.69 | 7.54 |
| S | 11.74 | 11.71 |
| Cl | 19.48 | 19.39 |

TABLE 5-16

Compound (11zc) (HCl salt)
$C_{17}H_{37}N_3S_2 \cdot 3HCl \cdot 3H_2O$ (FW = 511.05)

| | Calcd. (%): | Found (%): |
|---|---|---|
| C | 39.95 | 39.89 |
| H | 9.07 | 8.99 |
| N | 8.22 | 8.41 |
| S | 12.55 | 11.60 |
| Cl | 20.81 | 20.72 |

EXAMPLE 3

Preparation of
N,N'-bis[2-mercapto-2-methyl-1-(2-piperidinoethylamino)methylpropyl]ethylenediamine (14b)

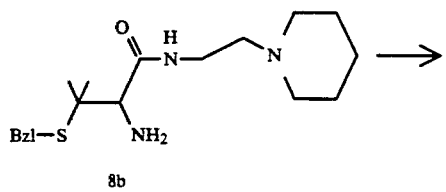
8b

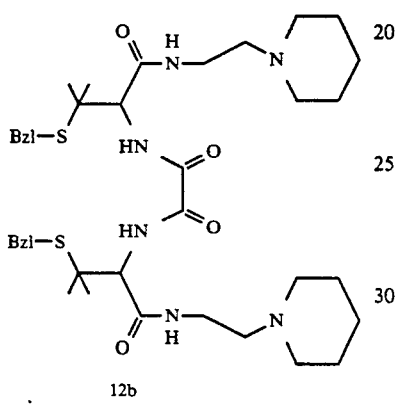
12b

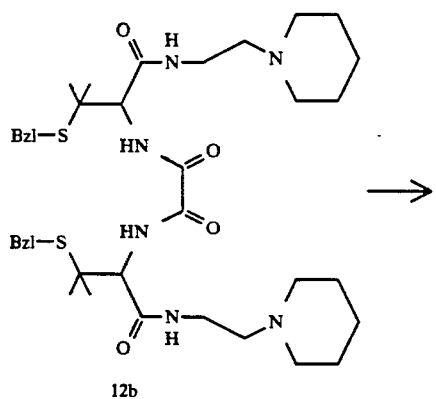
13b

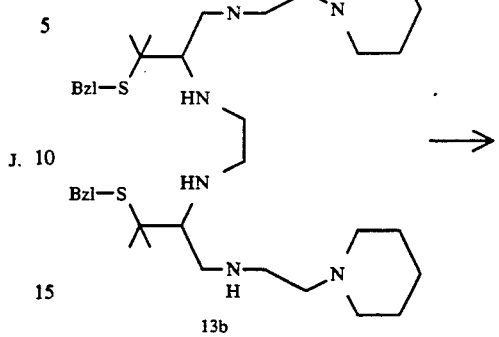
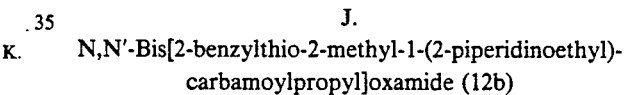
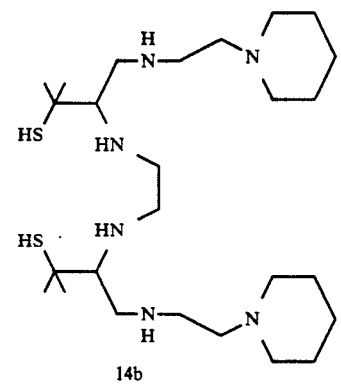
14b

J.
N,N'-Bis[2-benzylthio-2-methyl-1-(2-piperidinoethyl)-carbamoylpropyl]oxamide (12b)

To a solution of Compound (8b) (11.18 g; 32.0 mmol) in tetrahydrofuran (150 ml), triethylamine (20 ml; 144 mmol) was dropwise added while stirring at 0° C. A 4M oxalyl chloride solution in tetrahydrofuran (6.0 ml; 24 mmol) was dropwise added thereto, and the resultant mixture was stirred at the same temperature for 1 hour and at room temperature for 1 hour, followed by removal of insoluble materials by filtration. The filtrate was concentrated, ethyl acetate was added to the residue, and the resultant mixture was washed with a 1/30 N acetate buffer solution (pH, 5.9), a saturated aqueous sodium chloride solution, a 10% aqeuous potassium carbonate solution and a saturated aqueous sodium chloride solution in order three times. The organic layer was dried over anhydrous sodium sulfate and concentrated to give crude crystals. Recrystallization of the crude crystals from a mixture of ethyl acetate and ether gave Compound (12b) (7.14 g; yield, 57%).

K.
N,N'-Bis[2-benzylthio-2-methyl-1-(2-piperidinoethylamino)methylpropyl]ethylenediamine (13b)

In the same manner as in Example 1 H, Compound (13b) (3.95 g; 5.24 mmol) was reacted with diborane in tetrahydrofuran to give Compound (13b) (HCl salt) (4.34 g; yield, 90%).

L.

N,N'-Bis[2-mercapto-2-methyl-1-(2-piperidinoethylamino)methylpropyl]ethylenediamine (14b)

In the same manner as in Example 1 I, Compound (13b) (HCl salt) (1.83 g; 2 mmol) was subjected to Birch reduction to give Compound (14b) (HCl salt) (0.92 g; yield, 63%).

The IR and NMR analyses of Compound (14b) and the elementary analysis of Compound (14b) (HCl salt) are shown in Tables 6 and 7, respectively.

TABLE 6

Compound (14b)

IR (NaCl): $CH_3$ (2950 cm$^{-1}$), $CH_2$ (1460, 2925 cm$^{-1}$), $(CH_3)_2C=$ (1380 cm$^{-1}$), NH (3300 cm$^{-1}$), CH (1340 cm$^{-1}$).

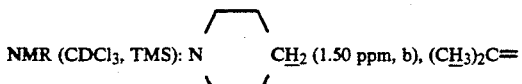

NMR (CDCl$_3$, TMS): N⟨CH$_2$⟩ (1.50 ppm, b), (C$\underline{H}_3$)$_2$C=
(1.40 ppm, s, 1.43 ppm, s), N$\underline{H}$ (2.09 ppm, s), C$\underline{H}_2$, C$\underline{H}$, S$\underline{H}$ (2.22–3.30 ppm).

TABLE 7

Compound (14b) (HCl salt)
$C_{26}H_{56}N_6S_2 \cdot 6HCl \cdot 3H_2O$ (FW = 789.70)

| | Calcd. (%): | Found (%): |
|---|---|---|
| C | 39.54 | 39.63 |
| H | 8.68 | 8.43 |
| N | 10.64 | 10.67 |
| S | 8.12 | 8.26 |
| Cl | 26.94 | 26.88 |

EXAMPLE 4

Preparation of polyaminedithiol compounds (Part II)

In the same manner as in Example 3 but replacing Compound (8b) having a side chain originated from 1-aminoethylpiperidine as the starting material by the corresponding compounds having a side chain originated from other amines, there were prepared 10 kinds of polyaminedithiol compounds (14a, 14p, 14q, 14r, 14s, 14t, 14u, 14x, 14y and 14d) as shown in Table 8 where the names of the starting amines and the yields (%) in each step from the starting compounds to the produced polyaminedithiol compounds are given. The names of the produced polyaminedithiol compounds, and their chemical structures and physical properties such as IR and NMR are given in Tables 9-1 to 9-10, and the data of their elementary analysis are given in Tables 10-1 to 10-10.

TABLE 8

| Amine | Product | Yield (%) |
|---|---|---|
| 1-Aminoethylpiperazine | 8a* | 100 |
| | 12a* | 50 |
| | 13a* | 52 |
| | 14a | 47 |
| 1-Aminoethyl-4-benzyl-piperazine | 8p | 68 |
| | 12p | 73 |
| | 13p | 91 |
| | 14p | 70 |
| 1-Aminoethyl-4-isopropyl-piperazine | 8q | 61 |
| | 12q | 73 |
| | 13q | 70 |
| | 14q | 85 |
| 1-Aminoethylmorpholine | 8r | 77 |
| | 12r | 44 |
| | 13r | 85 |

TABLE 8-continued

| Amine | Product | Yield (%) |
|---|---|---|
| | 14r | 95 |
| 1-(3-Aminopropyl)-morpholine | 8s | 75 |
| | 12s | 61 |
| | 13s | 91 |
| | 14s | 58 |
| N,N-Dimethylethylene-diamine | 8t | 66 |
| | 12t | 59 |
| | 13t | 79 |
| | 14t | 85 |
| N,N-Diethylethylene-diamine | 8u | 83 |
| | 12u | 37 |
| | 13u | 92 |
| | 14u | 89 |
| Propylamine | 8x | 84 |
| | 12x | 72 |
| | 13x | 69 |
| | 14x | 46 |
| Isobutylamine | 8y | 73 |
| | 12y | 52 |
| | 13y | 28 |
| | 14y | 54 |
| n-Amylamine | 8d | 91 |
| | 12d | 50 |
| | 13d | 46 |
| | 14d | 23 |

Note:
*These compounds were tosylated at the 4-position.

TABLE 9-1

N,N'-Bis[2-mercapto-2-methyl-1-(2-piperazinoethylamino)methylpropyl]-ethylenediamine (14a)

Structure:

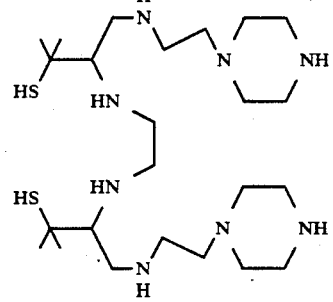

IR (NaCl): $CH_3$ (2950 cm$^{-1}$), $CH_2$ (1460, 2930 cm$^{-1}$), CH (1330 cm$^{-1}$), $(CH_3)_2C=$ (1210 cm$^{-1}$), NH (3300 cm$^{-1}$), SH (2540 cm$^{-1}$).
NMR (CDCl$_3$, TMS): (C$\underline{H}_3$)$_2$C= (1.34 ppm, s, 1.43 ppm, s), N$\underline{H}$ (2.10 ppm, s), C$\underline{H}$, C$\underline{H}_2$, S$\underline{H}$ (2.24–3.30 ppm).

TABLE 9-2

N,N'-Bis[1-(2-(4-benzylpiperazino)-ethylamino)methyl-2-mercapto-2-methyl-propyl]ethylenediamine (14p)

Structure:

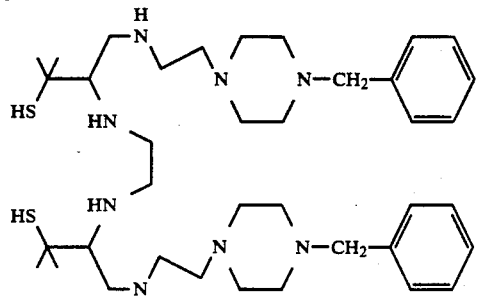

IR (NaCl): $CH_3$ (2950 cm$^{-1}$), $CH_2$ (1460, 2930 cm$^{-1}$), CH (1330 cm$^{-1}$), $(CH_3)_2C=$ (1210 cm$^{-1}$), $C_6H_5$ (1590, 3030 cm$^{-1}$), NH (3300 cm$^{-1}$), SH (2540 cm$^{-1}$).

TABLE 9-2-continued

NMR (CDCl₃, TMS): (C$\underline{H}_3$)₂C= (1.38 ppm, b), N$\underline{H}$ (2.10 ppm, s), 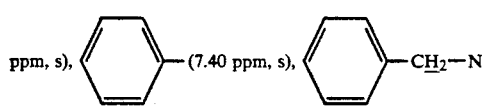

(3.80 ppm, s), C$\underline{H}$, C$\underline{H}_2$, S$\underline{H}$ (2.24–3.30 ppm).

TABLE 9-3

N,N'-Bis[1-(2-(4-isopropylpiperazino)-ethylamino)methyl-2-mercapto-2-methyl-propyl]ethylenediamine (14q)

Structure:

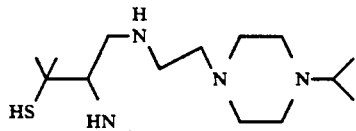

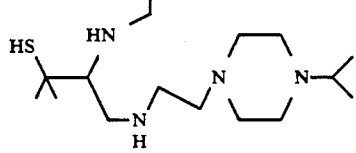

IR (NaCl): CH₃ (2960 cm⁻¹), CH₂ (1460, 2925 cm⁻¹), CH (1340, 2890 cm⁻¹), (CH₃)₂CH (1170, 1380 cm⁻¹), NH (3300 cm⁻¹), SH (2540 cm⁻¹).
NMR (CDCl₃, TMS): (C$\underline{H}_3$)₂CH (1.05 ppm, d), (C$\underline{H}_3$)₂C= (1.39 ppm, s), N$\underline{H}$(1.90 ppm, s), C$\underline{H}$, C$\underline{H}_2$, S$\underline{H}$ (2.12–3.18 ppm).

TABLE 9-4

N,N'-Bis[2-mercapto-2-methyl-1-(2-morpholinoethylamino)methyl-propyl]-ethylenediamine (14r)

Structure:

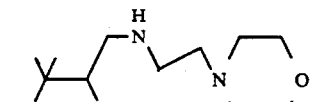

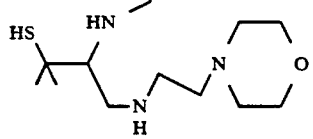

IR (NaCl): CH₃ (2965 cm⁻¹), CH₂ (1460, 2925 cm⁻¹), CH (1340, 2899 cm⁻¹), (CH₃)₂C= (1385 cm⁻¹), NH (3300 cm⁻¹), SH (2540 cm⁻¹),  O (1120 cm⁻¹).

NMR (CDCl₃, TMS): (C$\underline{H}_3$)₂C= (1.42 ppm, s, 1.50 ppm, s),

N$\underline{H}$ (1.95 ppm, s), 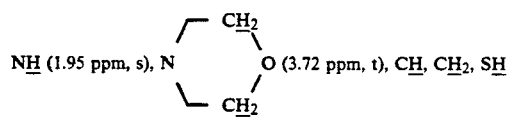 (3.72 ppm, t), C$\underline{H}$, C$\underline{H}_2$, S$\underline{H}$ (2.20–3.30 ppm).

TABLE 9-5

N,N'-Bis[2-mercapto-2-methyl-1-(3-morpholinopropylamino)methyl-propyl]ethylenediamine (14s)

Structure:

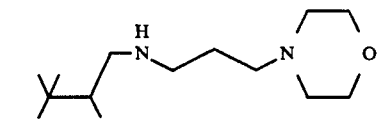

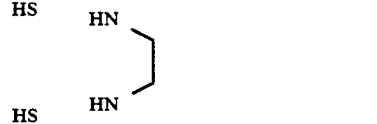

IR (NaCl): CH₃ (2965 cm⁻¹), CH₂ (1460, 2925 cm⁻¹), CH (1340, 2899 cm⁻¹), (CH₃)₂C= (1385 cm⁻¹), NH (3300 cm⁻¹), SH (2540 cm⁻¹), N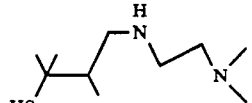O (1120 cm⁻¹).

NMR (CDCl₃, TMS): (C$\underline{H}_3$)₂C= (1.43 ppm, s),
NHCH₂C$\underline{H}_2$CH₂CH₃ (1.79 ppm, m), N$\underline{H}$ (1.99 ppm, s), N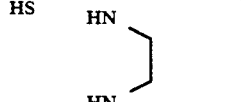O (3.73 ppm, t), C$\underline{H}$, C$\underline{H}_2$, S$\underline{H}$ (2.20–3.34 ppm).

TABLE 9-6

N,N'-Bis[2-mercapto-2-methyl-1-(2-(N,N-dimethylamino)ethylamino)-methyl-propyl]ethylenediamine (14t)

Structure:

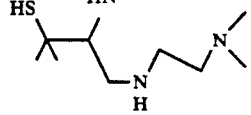

IR (NaCl): CH₃ (2975 cm⁻¹), CH₂ (1460, 2940 cm⁻¹), CH (2870 cm⁻¹), (CH₃)₂C= (1380 cm⁻¹), NH (3300 cm⁻¹), SH (2550 cm⁻¹).
NMR (CDCl₃, TMS): (C$\underline{H}_3$)₂N (2.18 ppm, s), (C$\underline{H}_3$)₂C= (1.35 ppm, s, 1.39 ppm, s), N$\underline{H}$ (1.90 ppm, s), C$\underline{H}$, C$\underline{H}_2$, S$\underline{H}$ (2.34–3.20 ppm).

TABLE 9-7

N,N'-Bis[1-2-(N,N-diethylamino) ethylamino)methyl-2-mercapto-2-methylpropyl]ethylenediamine (14u)

TABLE 9-7-continued

Structure:

IR (NaCl): CH$_3$ (2975 cm$^{-1}$), CH$_2$ (1460, 2925 cm$^{-1}$), CH (2890 cm$^{-1}$), (CH$_3$)$_2$C= (1380 cm$^{-1}$), NH (3300 cm$^{-1}$), SH (2500 cm$^{-1}$).
NMR (CDCl$_3$, TMS): N(CH$_2$C<u>H</u>$_3$)$_2$ (1.02 ppm, t), (C<u>H</u>$_3$)$_2$C= (1.39 ppm, s, 1.42 ppm, s), N<u>H</u> (1.94 ppm, s), C<u>H</u>, C<u>H</u>$_2$, S<u>H</u> (2.20–3.20 ppm).

TABLE 9-8

N,N'-Bis(2-mercapto-2-methyl-1-propylaminopropyl)ethylenediamine (14x)

Structure:

IR (NaCl): CH$_3$ (2975 cm$^{-1}$), CH$_2$ (1460, 2925 cm$^{-1}$), CH (1340, 2899 cm$^{-1}$), (CH$_3$)$_2$C= (1380 cm$^{-1}$), NH (3300 cm$^{-1}$), SH (2540 cm$^{-1}$).
NMR (CDCl$_3$, TMS): NHCH$_2$CH$_2$C<u>H</u>$_3$ (0.94 ppm, t), (C<u>H</u>$_3$)$_2$C= (1.41 ppm, s, 1.43 ppm, s), N<u>H</u> (1.92 ppm, s), C<u>H</u>, C<u>H</u>$_2$, S<u>H</u> (2.30–3.10 ppm).

TABLE 9-9

N,N'-Bis(1-isobutylaminomethyl-2-mercapto-2-methylpropyl)ethylenediamine (14y)

Structure:

IR (NaCl): CH$_3$ (2960 cm$^{-1}$), CH$_2$ (1460, 2925 cm$^{-1}$), CH (1340, 2890 cm$^{-1}$), (CH$_3$)$_2$CH (1170, 1380 cm$^{-1}$), NH (3300 cm$^{-1}$), SH (2540 cm$^{-1}$).
NMR (CDCl$_3$, TMS): (C<u>H</u>$_3$)$_2$CH (0.93 ppm, d), (C<u>H</u>$_3$)$_2$C= (1.41 ppm, s, 1.45 ppm, s), N<u>H</u> (1.82 ppm, s), C<u>H</u>, C<u>H</u>$_2$, S<u>H</u> (2.21–3.13 ppm).

TABLE 9-10

N,N'-Bis[1-n-amylaminomethyl-2-mercaptp-2-methylpropyl]ethylenediamine (14d)

Structure:

IR (NaCl): CH$_3$ (2960 cm$^{-1}$), CH$_2$ (1460, 2930 cm$^{-1}$), CH (2860 cm$^{-1}$), (CH$_3$)$_2$C= (1160, 1380 cm$^{-1}$), NH (3300 cm$^{-1}$), SH (2540 cm$^{-1}$).
NMR (CDCl$_3$, TMS): NH(CH$_2$)$_4$C<u>H</u>$_3$ (0.91 ppm, t), (C<u>H</u>$_3$)$_2$C=, NH(CH$_2$)$_2$C<u>H</u>$_2$C<u>H</u>$_2$CH$_3$ (1.10–1.85 ppm), N<u>H</u> (1.05 ppm, s), C<u>H</u>, C<u>H</u>$_2$, S<u>H</u> (2.25–3.10 ppm).

TABLE 10-1

Compound (14a) (HCl salt)
$C_{24}H_{54}N_8S_2 \cdot 8HCl \cdot 2H_2O$ (FW = 846.58)

| | Calcd. (%): | Found (%): |
|---|---|---|
| C | 34.05 | 34.17 |
| H | 7.86 | 7.63 |
| N | 13.24 | 13.34 |
| S | 7.57 | 7.42 |
| Cl | 33.50 | 33.48 |

TABLE 10-2

Compound (14p) (HCl salt)
$C_{38}H_{66}N_8S_2 \cdot 8HCl \cdot 3H_2O$ (FW = 1044.85)

| | Calcd. (%): | Found (%): |
|---|---|---|
| C | 43.68 | 43.59 |
| H | 7.72 | 7.85 |
| N | 10.72 | 10.68 |
| S | 6.14 | 6.20 |
| Cl | 27.15 | 27.21 |

TABLE 10-3

Compound (14q) (HCl salt)
$C_{20}H_{66}N_8S_2 \cdot 6HCl \cdot H_2O$ (FW = 719.67)

| | Calcd. (%): | Found (%): |
|---|---|---|
| C | 33.38 | 33.19 |
| H | 10.36 | 10.51 |
| N | 15.57 | 15.49 |
| S | 8.91 | 8.99 |
| Cl | 29.56 | 29.58 |

TABLE 10-4

Compound (14r) (HCl salt)
$C_{24}H_{50}N_6S_2 \cdot 6HCl \cdot 4H_2O$ (FW = 777.65)

| | Calcd. (%): | Found (%): |
|---|---|---|
| C | 37.07 | 36.89 |
| H | 8.30 | 8.53 |
| N | 10.81 | 10.92 |
| S | 8.25 | 8.31 |
| Cl | 27.35 | 27.32 |

TABLE 10-5

Compound (14s) (HCl salt)
$C_{26}H_{52}N_6S_2 \cdot 6HCl \cdot 5H_2O$ (FW = 821.70)

|   | Calcd. (%): | Found (%): |
|---|---|---|
| C | 38.00 | 37.92 |
| H | 8.34  | 8.51  |
| N | 10.23 | 10.21 |
| S | 7.80  | 7.73  |
| Cl| 25.89 | 25.83 |

TABLE 10-6

Compound (14t) (HCl salt)
$C_{20}H_{43}N_6S_2 \cdot 6HCl \cdot 3/2H_2O$ (FW = 677.51)

|   | Calcd. (%): | Found (%): |
|---|---|---|
| C | 35.46 | 35.43 |
| H | 7.74  | 7.80  |
| N | 12.40 | 12.45 |
| S | 9.46  | 9.43  |
| Cl| 31.40 | 31.40 |

TABLE 10-7

Compound (14u) (HCl salt)
$C_{24}H_{56}N_6S_2 \cdot 6HCl \cdot 3/2H_2O$ (FW = 738.66)

|   | Calcd. (%): | Found (%): |
|---|---|---|
| C | 39.03 | 39.10 |
| H | 8.87  | 8.85  |
| N | 11.38 | 11.42 |
| S | 8.68  | 8.70  |
| Cl| 28.80 | 28.82 |

TABLE 10-8

Compound (14 x) (HCl salt)
$C_{18}H_{42}N_4S_2 \cdot 4HCl \cdot 2H_2O$ (FW = 560.55)

|   | Calcd. (%): | Found (%): |
|---|---|---|
| C | 38.57 | 38.54 |
| H | 8.99  | 9.03  |
| N | 9.99  | 9.95  |
| S | 11.44 | 11.45 |
| Cl| 25.30 | 25.23 |

TABLE 10-9:

Compound (14 y) (HCl salt)
$C_{20}H_{46}N_4S_2 \cdot 4HCl \cdot \frac{1}{2}H_2O$ (FW = 561.59)

|   | Calcd. (%): | Found (%): |
|---|---|---|
| C | 42.78 | 42.64 |
| H | 9.15  | 9.08  |
| N | 9.98  | 9.82  |
| S | 11.42 | 11.69 |
| Cl| 25.25 | 25.31 |

TABLE 10-10

Compound (14 d) (HCl salt)
$C_{22}H_{50}N_4S_2 \cdot 4HCl \cdot 3H_2O$ (FW = 634.72)

|   | Calcd. (%): | Found (%): |
|---|---|---|
| C | 41.63 | 41.82 |
| H | 9.53  | 9.44  |
| N | 8.83  | 8.79  |
| S | 10.10 | 10.08 |
| Cl| 22.34 | 22.53 |

EXAMPLE 5

Preparation of N,N'-Bis(1-aminomethyl-2-mercapto-2-methylpropyl)ethylenediamine (19)

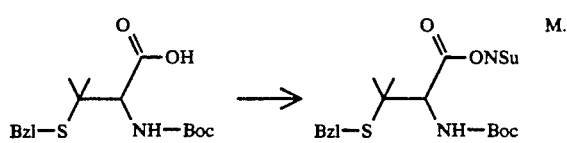

M.

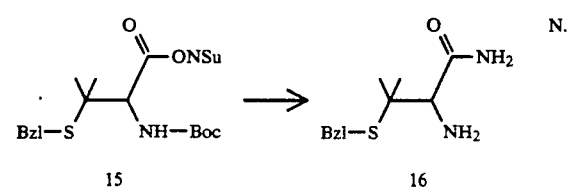

N.

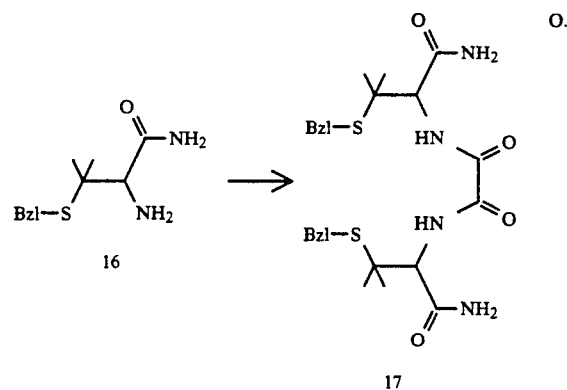

O.

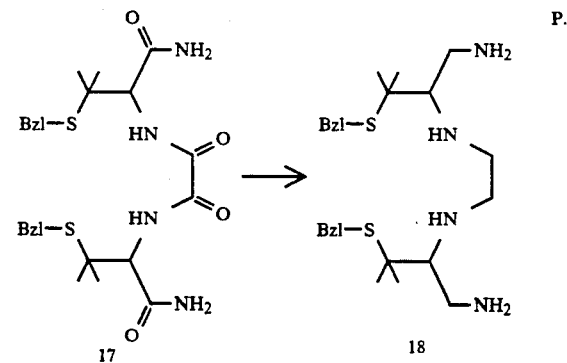

P.

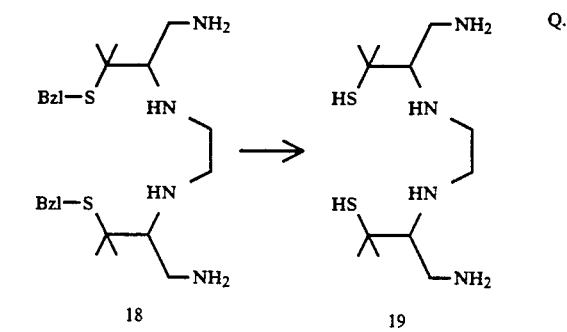

Q.

M. S-Benzyl-Boc-D-penicillamine succinimide ester (15)

To a solution of Compound (7) (2.38 g; 7 mmol) and N-hydroxysuccinimide (0.805 g; 7 mmol) in dimethylformamide (10 mmol), dicyclohexylcarbodiimide (1.5 g; 7.7 mmol) was added at 0° C. The resultant mixture was stirred at the same temperature for 20 minutes and at room temperature for 40 minutes, followed by removal of insoluble materials by filtraton. The resulting mixture was concentrated, combined with ethyl acetate and washed with 10% aqueous citric acid, a saturated aqueous sodium chloride solution, a saturated sodium hydrogen carbonate solution and a saturated aqueous sodium chloride solution in order two times. The organic layer was separated, dried over anhydrous sodium sulfate and concentrated to give Compound (15) (3.58 g; yield, 100%).

N. S-Benzyl-D-penicillamine amide (16)

To a solution of Compound (15) (437 mg; 1 mmol) in ethyl acetate (5 ml), 28% aqueous ammonia (10 ml; 164 mmol) was dropwise added at 0° C., followed by stirring overnight. The reaction mixture was combined with ethyl acetate, washed with 10% aqueous citric acid (×3), a saturated aqueous sodium chloride solution (×3), a saturated sodium hydrogen carbonate solution (×1) and a saturated aqueous sodium chloride solution (×1) in order and dried over anhydrous sodium sulfate. To the residue, a 25% hydrogen bromide solution in acetic acid (6.31 g; 20 mmol) was added. The resultant mixture was stirred at 0° C. for 3 hours and concentrated. The residue was combined with water and adjusted to pH 11 with potassium carbonate, followed by extraction with chloroform three times. The extract was dried over anhydrous sodium sulfate and concentrated to give Compound (16) (255 mg; yield, 97%).

O. N,N'-Bis(2-benzylthio-1-carbamoyl-2-methylpropyl-)oxamide (17)

In the same manner as in Example 3 J but using Compound (16) (1.19 g; 5 mmol) and a 4M oxalyl chloride solution in tetrahydrofuran (0.94 ml; 3.76 mmol), there was obtained Compound (17) (0.63 g; yield, 47%).

P. N,N'-Bis(1-aminomethyl-2-benzylthio-2-methylpropyl-)ethylenediamine (18)

In the same manner as in Example 1 H but using Compound (17) (531 mg; 1 mmol) and a 1M diborane solution in tetrahydrofuran (40 ml; 40 mmol), there was obtained Compound (18) (300 mg; yield, 48%).

Q. N,N'-Bis(1-aminomethyl-2-mercapto-2-methylpropyl-)ethylenediamine (19)

In the same manner as in Example 1 I but using Compound (18) (2.00 g; 3.22 mmol), there was obtained Compound (19) (HCl salt) (275 mg; yield, 19%).

The IR and NMR analyses of Compound (19) and the elementary analysis of Compound (19) (HCl salt) are respectively shown in Tables 11-1 and 11-2.

TABLE 11-1

Compound (19)

IR (NaCl): CH$_3$ (2950 cm$^{-1}$), CH$_2$ (1460, 2925 cm$^{-1}$), (CH$_3$)$_2$C = (1210 cm$^{-1}$), NH (3300 cm$^{-1}$), SH (2540 cm$^{-1}$).

TABLE 11-1-continued

Compound (19)

NMR (CDCl$_3$, TMS): (CH$_3$)$_2$C = (1.39 ppm, s), NH (1.97 ppm, s), CCH, CH$_2$, SH$_{(2.20-3.30\ ppm)}$.

TABLE 11-2

Compound (19) (HCl salt)
C$_{12}$H$_{30}$N$_4$S$_2$.4HCl.3H$_2$O (FW = 494.41)

|   | Calcd. (%): | Found (%): |
|---|---|---|
| C | 29.15 | 29.03 |
| H | 8.15 | 8.21 |
| N | 11.33 | 11.30 |
| S | 12.97 | 12.85 |
| Cl | 28.63 | 28.51 |

EXAMPLE 6

Preparation of N-(2-mercapto-2-methyl-1-morpholinomethylpropyl)-N'-(1-isopropylaminomethyl-2-mercapto-2-methylpropyl)ethylenediamine (23ck)

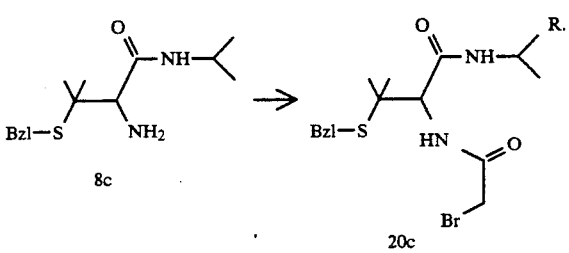

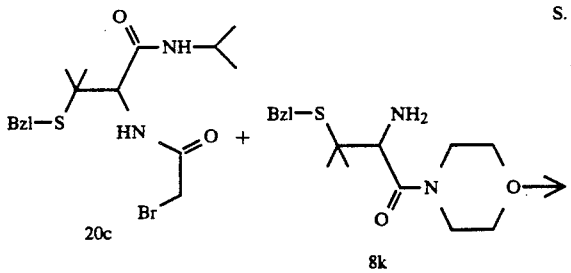

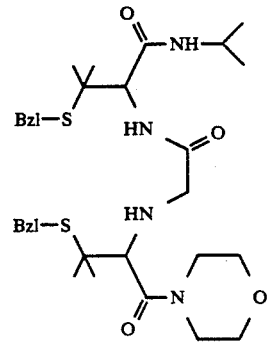

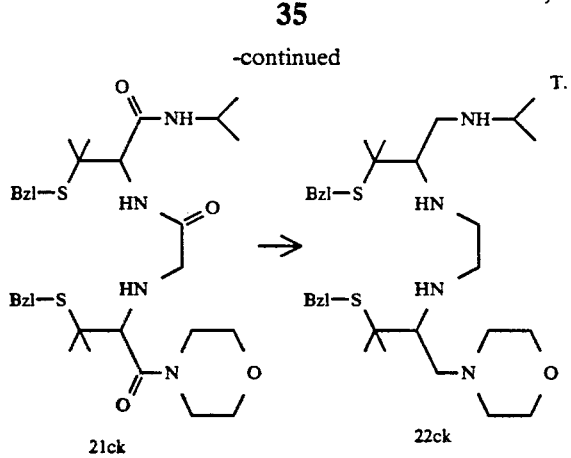

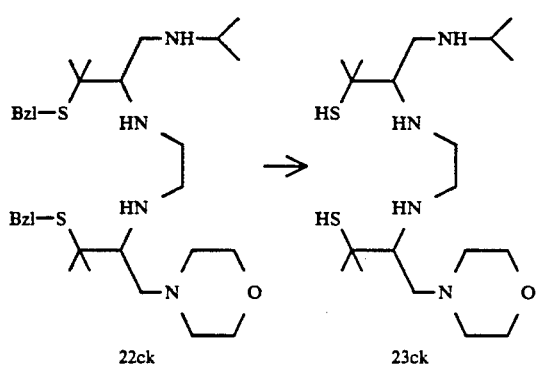

R. S-Benzyl-N-bromoacetyl-D-penicillamine isopropylamide (20c)

To a solution of Compound (8c) (2.79 g; 10 mmol) in tetrahydrofuran, triethylamine (2.59 ml; 20 mmol) was dropwise added at 0° C., followed by dropwise addition of bromoacetyl chloride (0.91 ml; 11 mmol). The resultant mixture was stirred at the same temperature for 1 hour and at room temperature for 1 hour. After removal of insoluble materials, the reaction mixture was concentrated, and the residue was combined with ethyl acetate. The resulting mixture was washed with 10% aqueous citric acid, water, a saturated aqueous sodium hydrogen carbonate solution and water in order three times. The organic layer was collected, dried over anhydrous sodium sulfate and concentrated to give Compound (20c) (3.60 g; yield, 90%).

S. N-(2-Benzylthio-2-methyl-1-morpholinocarbonyl-propyl)glycyl-S-benzyl-D-penicillamine isopropylamide (21ck)

To a solution of Compound (20c) (2.00 g; 5 mmol) and Compound (8k) (1.70 g; 5.5 mmol) in toluene (20 ml), sodium methoxide (0.30 g; 5.5 mmol) was added, and the resultant mixture was refluxed for 24 hours. The reaction mixture was washed with 10% aqueous citric acid and water in order three times, dried over anhydrous sodium sulfate and concentrated, followed by crystallization from a mixture of ethyl acetate, ether and hexane. The precipitated crystals were recrystallized from a mixture of ethyl acetate, ether and hexane to give Compound (21ck) (2.14 g; yield, 62%).

T. N-(2-Benzylthio-2-methyl-1-morpholinomethylpropyl)-N'-(2-benzylthio-1-isopropylaminomethyl-2-methylpropyl)ethylenediamine (22ck)

In the same manner as in Example 1 H but using Compound (21ck) (1.88 g; 3 mmol) and a 1M diborane solution in tetrahydrofuran (12 ml; 12 mmol), there was obtained Compound (22ck) (HCl salt) (1.76 g; yield, 80%).

U. N-(2-Mercapto-2-methyl-1-morpholinomethylpropyl)—N'-(1-isopropylaminomethyl-2-mercapto-2-methylpropyl)ethylenediamine (23ck)

In the same manner as in Example 1 I but using Compound (22ck) (732 mg; 1 mmol), there was obtained Compound (23ck) (HCl salt) (387 mg; yield, 75%).

The IR and NMR analyses of Compound (23ck) and the elementary analysis of Compound (23ck) (HCl salt) are respectively shown in Tables 12 and 13.

TABLE 12

Compound (23ck)

IR (NaCl): $CH_3$ (2965 $cm^{-1}$), $CH_2$ (1460, 2925 $cm^{-1}$), CH (1340, 2899 $cm^{-1}$), $(CH_3)_2C=$ (1385 $cm^{-1}$), NH (3300

$cm^{-1}$), SH (2540 $cm^{-1}$), N◯O (1120 $cm^{-1}$), $(CH_3)_2CH$ (1170, 1380 $cm^{-1}$).
NMR ($CDCl_3$, TMS): $(C\underline{H}_3)_2C=$ (1.39 ppm, s), N$\underline{H}$

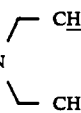

(2.00 ppm, s), N◯O (3.72 ppm, t), $(C\underline{H}_3)_2CH$ (1.08 ppm, d), C$\underline{H}$, C$\underline{H}_2$, S$\underline{H}$ (2.43–3.20 ppm).

TABLE 13

| Compound (23 ck) (HCl salt) $C_{19}H_{42}N_4S_2 \cdot 4HCl \cdot 3/2H_2O$ (FW = 563.56) | | |
|---|---|---|
| | Calcd. (%): | Found (%): |
| C | 40.49 | 40.52 |
| H | 8.76 | 8.69 |
| N | 9.94 | 9.99 |
| S | 11.38 | 11.38 |
| Cl | 25.16 | 25.13 |

EXAMPLE 7

N-(2-Butylthio-2-methylpropyl)-N'-(2-mercapto-2-methyl-1-(4-methylpiperidino)methylpropyl)ethylenediamine (33)

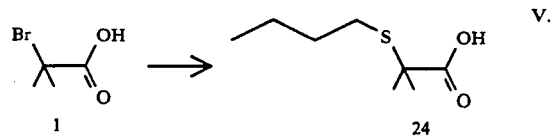

-continued
W.
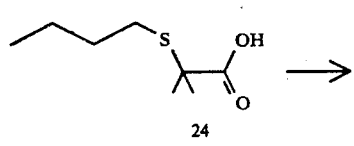
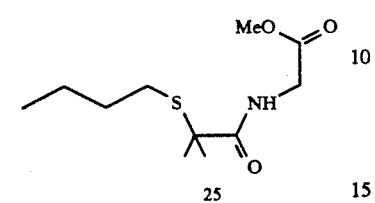
X.
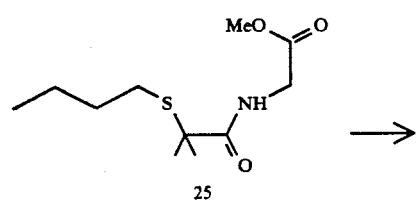
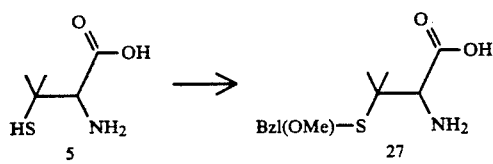
Y.
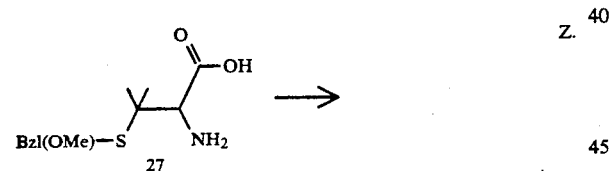
Z.
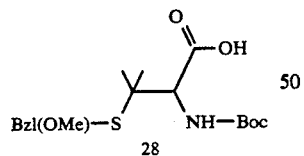
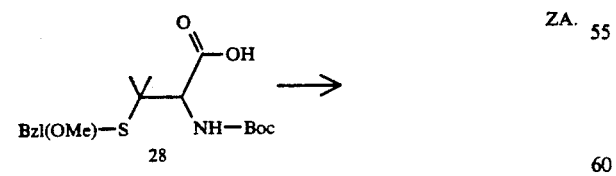
ZA.
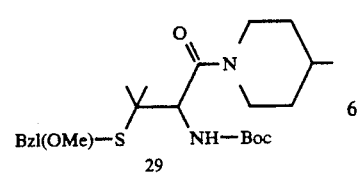
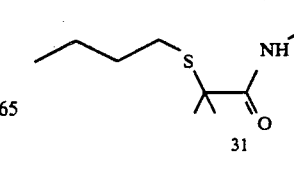
-continued
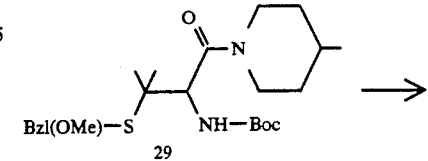
ZB.
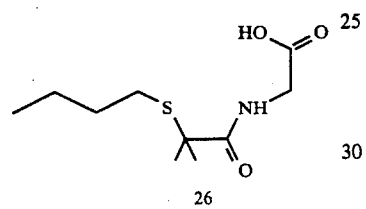
ZC.
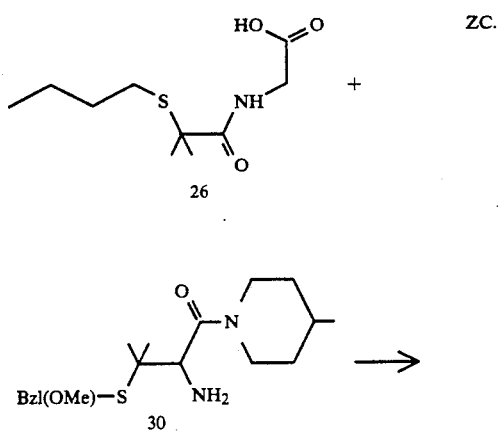
ZD.
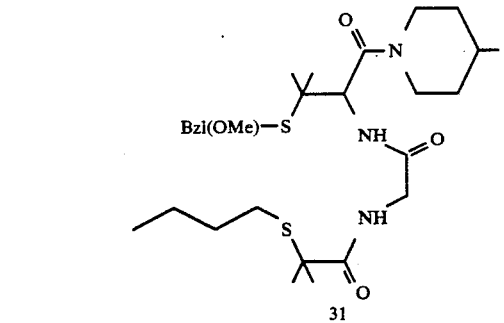
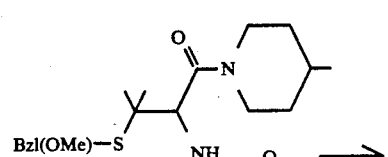

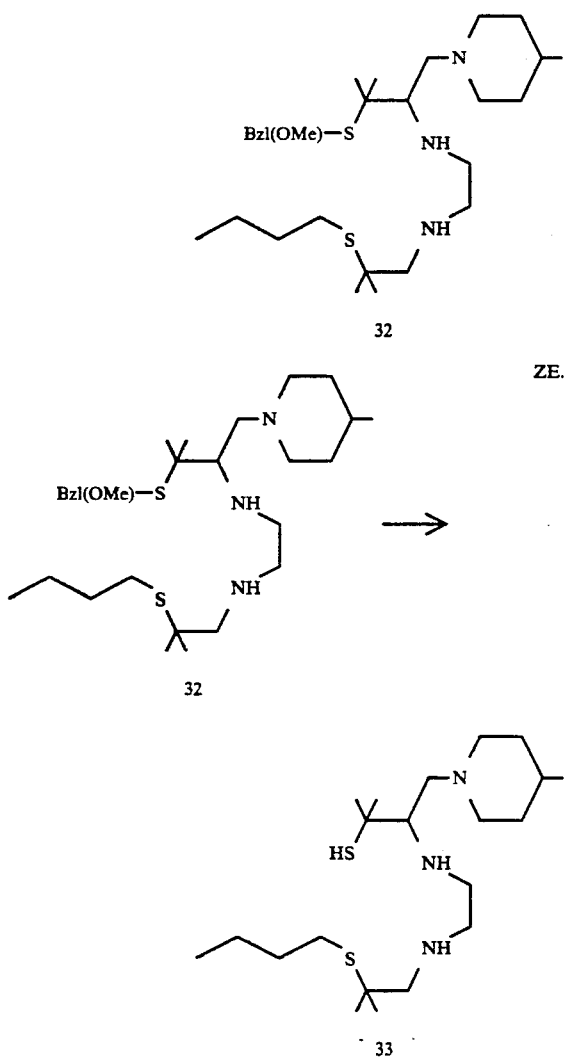

V. Butylthioisobutyric acid (24)

Butylmercaptan (216 ml; 2.0 mol) was added to isopropanol (460 ml), and under cooling, 6.5 N aqueous sodium hydroxide (460 ml) and an isopropanol solution (460 ml) containing bromoisobutyric acid (167 g; 1.77 mol) were added thereto in order. The reaction mixture was heated to 80° C. and stirred for 44 hours, followed by allowing to react at room temperature overnight. The reaction mixture was combined with water (460 ml) and adjusted to pH 9 with a 6N hydrochloric acid under cooling. The mixture was washed with n-hexane three times. The aqueous layer was adjusted to pH 3 with a 6N hydrochloric acid under cooling and extracted with ethyl acetate two times. The organic layer was washed with water and a saturated aqueous sodium chloride solution, dried over anhydrous sodium sulfate and concentrated to give the objective compound (24) as an oil (165 g; yield, 93%).

W. 2-Butylthio-2-methylpropionylglycine methyl ester (25)

To a suspension of glycine methyl ester hydrochloride (25.1 g; 200 mmol) in chloroform (160 ml), triethylamine (28 ml; 200 mmol) was added under cooling. Compound (24) (35.5 g; 200 mmol) in chloroform (40 ml) was added thereto, followed by dropwise addition of dicyclohexylcarbodiimide (45.4 g; 220 mmol) in chloroform. The resultant mixture was stirred under cooling for 1 hour and at room temperature overnight. After removal of insoluble materials, the reaction mixture was concentrated and combined with ethyl acetate, followed by removal of insoluble materials. The organic layer was washed with 5% an aqueous sodium hydrogen carbonate solution, water, 1N hydrochloric acid, water and a saturated aqueous sodium chloride solution in order. The organic layer was collected, dried over anhydrous sodium sulfate and concentrated. The residue was purified by silica gel column chromatography with a mixture of hexane and acetone (10:1) as an eluting solvent to give Compound (25) as an oil (7.7 g; yield, 15%).

X. 2-Butylthio-2-methylpropionylglycine (26)

To a solution of Compound (25) (7.7 g; 30 mmol) in methanol (70 ml), 1N sodium hydroxide solution (33 ml; 33mmol)) was added under cooling, and the resultant mixture was stirred at the same temperature for 1 hour and at room temperature for 4 hours, followed by concentration. The residue was washed with ether. The aqueous layer was adjusted to pH 3 with citric acid under cooling and saturated with sodium chloride, followed by extraction with ethyl acetate. The extract was washed with a saturated aqueous sodium chloride solution, dried over anhydrous sodium sulfate and concentrated to give Compound (26) as an oil (4.2 g; yield, 59%).

Y. S-Methoxybenzyl-D-penicillamine (27)

To a suspension of D-Penicillamine (99.7 g; 668 mmol) in a mixture of oxygen-free isopropanol (590 ml) and oxygen-free water (470 ml), triethylamine (187 ml; 1330 mmol) was added under cooling. To the resultant suspension, p-methoxybenzyl chloride (136 g; 868 mmol) was dropwise added, and the mixture was stirred at room temperature overnight. The reaction mixture was combined with water (1000 ml), adjusted to pH 3 with 3N hydrochloric acid and allowed to stand under cooling. The precipitated crystals were collected by filtration and washed with water to give Compound (27) (174 g; yield, 97%).

Z. S-Methoxybenzyl-Boc-D-penicillamine (28)

To a suspension of Compound (27) (182 g; 676 mmol) in methanol (900 ml), triethylamine (94.7 ml; 676 mmol) was added under cooling. di-t-Butyl dicarbonate (177 g; 811 mmol) in methanol (250 ml) was dropwise added thereto, and the resultant mixture was stirred at room temperature overnight. The reaction mixture was concentrated, combined with water and, after removal of insoluble materials by filtration, washed with ether. The aqueous layer was adjusted to pH 5 with citric acid and extracted with ethyl acetate. The extract was washed with water and a saturated aqueous sodium chloride solution in order three times, dried over anhydrous sodium sulfate and concentrated. The precipitated crystals were collected by filtration to give Compound (28) (157 g; yield, 63%).

ZA.
N-t-Butoxycarbonyl-2-p-methoxybenzylthio-2-methyl-1-(4-methylpiperidino)carbonylpropylamine (29)

To a solution of Compound (28) (29.6 g; 80.0 mmol) and 4-methylpiperidine (10.4 ml; 88.0 mmol) in tetrahydrofuran (100 ml), 1-hydroxybenzotriazole (16.2 g; 120 mmol) was added under cooling. Dicyclohexylcarbodiimide (18.2 g; 88.0 mmol) in tetrahydrofuran (50 ml) was dropwise added thereto, and the resultant mixture was stirred under cooling for 1 hour and at room temperature for 4 hours. After removal of insoluble materials by filtration, the filtrate was concentrated and combined with ethyl acetate. The resulting mixture was washed with 10% citric acid, a saturated aqueous sodium chloride solution, a saturated aqueous sodium hydrogen carbonate solution and a saturated sodium chloride solution in order three times. The organic layer was collected, dried over anhydrous sodium sulfate and concentrated to give Compound (29) (36.0 g; yield, 100%).

ZB.
2-p-Methoxybenzylthio-2-methyl-1-(4-methylpiperidino)carbonylpropylamine (30)

Compound (29) (36.0 g; 80.0 mmol) was dissolved in a 4N hydrogen chloride solution in dioxane (400 ml; 1600 mmol) under cooling, and the resulting mixture was stirred at room temperature overnight. The reaction mixture was concentrated and washed with petroleum ether by decantation, followed by concentration to give Compound (30) (HCl salt) (30.8 g; yield, 100%).

ZC.
N-(2-Butylthio-2-methylpropionylglycyl)-2-p-methoxy-2-methyl-1-(4-methylpiperidino)carbonylpropylamine (31)

To a suspension of Compound (30) (HCl salt) (7.7 g; 20.0 mmol) in tetrahydrofuran (30 ml), triethylamine (2.8 ml; 20 mmol) was added under cooling, followed by addition of Compound (26) (4.2 g; 18 mmol) and 1-hydroxybenzotriazole (3.6 g; 27 mmol). Dicyclohexylcarbodiimide (4.1 g; 20 mmol) in tetrahydrofuran (20 ml) was dropwise added thereto, and the resultant solution was stirred under cooling for 1 hour and at room temperature for 3 hours. After removal of insoluble materials by filtration, the filtrate was concentrated, combined with ethyl acetate and washed with 10 citric acid, a saturated aqueous sodium chloride solution, a saturated aqueous sodium hydrogen carbonate solution and a saturated aqueous sodium chloride solution in order three times. The organic layer was collected, dried over anhydrous sodium sulfate and concentrated. The residue was purified by silica gel column chromatography with dichloromethane as an eluting solvent to give Compound (31) (7.4 g; yield, 72%) as an oil.

ZD.
N-(2-Butylthio-2-methylpropyl)-N'-[2-p-methoxybenzylthio-2-methyl-1-(4-methylpiperidino)methylpropyl]ethylenediamine (32)

To a suspension of Compound (31) (6.00 g; 10.5 mmol) in tetrahydrofuran (60 ml), lithium aluminium hydride (2.00 g; 52.5 mmol) was added under cooling. The resultant mixture was stirred at room temperature for 3 hours and at 65° C. for 4 hours. After dropwise addition of 6N hydrochloric acid (42 ml; 252 mmol) under cooling, water was added to the reaction mixture. The resultant mixture was washed with ether three times, adjusted to pH 11 with potassium carbonate and extracted with chloroform three times. The chloroform extract was washed with a saturated aqueous sodium chloride solution, dried over anhydrous sodium sulfate and concentrated. Under cooling, a 4N hydrogen chloride in dioxane (160 ml; 63 mmol) was added thereto. The resultant mixture was again concentrated. The residue was purified by silica gel column chromatography with a mixture of chloroform and methanol (20:1) as an eluting solvent to give Compound (32) (HCl salt) (4.1 g; yield, 65%).

ZE.
N-(2-Butylthio-2-methylpropyl)-N'-[2-mercapto-2-methyl-1-(4-methylpiperidino)methylpropyl]ethylenediamine (33)

A solution of Compound (32) (HCl salt) (2.5 g; 4.2 mmol) in a 1M trifluoromethanesulfonic acid in tetrahydrofuran (42 ml; 42 mmol) was stirred for 1 hour under cooling. The reaction mixture was combined with ether and extracted with 2N hydrochloric acid five times. The aqueous layer was adjusted to pH 10 with potassium carbonate and extracted with chloroform three times. The chloroform extract was washed with a saturated aqueous sodium chloride solution two times, dried over anhydrous sodium sulfate and concentrated. Under cooling, a 4N hydrogen chloride in dioxane (7 ml; 28 mmol) was added thereto, followed by concentration. The residue was purified by silica gel column chromatography with a mixture of chloroform and methanol (20:1) as an eluting solvent to give Compound (33) (HCl salt) (0.5 g; yield, 24%).

Compound (33) (HCl salt) (20 mg) was adjusted to pH 11 with addition of 10% aqueous potassium carbonate solution and extracted with chloroform three times. The chloroform extract was washed with a saturated aqueous sodium chloride solution two times, dried over anhydrous sodium sulfate and concentrated. The residue was subjected to IR and NMR analyses, and the results are given in Table 14. The HCl salt of Compound (33) was subjected to an elementary analysis, and the results are shown in Table 15.

TABLE 14

IR (NaCl): $CH_3$ (2910 cm$^{-1}$), $CH_2$ (1460, 2860 cm$^{-1}$), CH (1360, 2730 cm$^{-1}$), $(CH_3)_2C=$ (1380 cm$^{-1}$), NH (3300 cm$^{-1}$), SH (2550 cm$^{-1}$).
NMR (CDCl$_3$, TMS): (C$\underline{H}_3$)$_5$C= (1.25 ppm, s, 1.33 ppm, s), N$\underline{H}$ (2.05 ppm, s), C$\underline{H}$, C$\underline{H}_2$, S$\underline{H}$ (2.22–2.90 ppm).

TABLE 15

Compound (33) (HCl salt)
$C_{21}H_{45}N_3S_2 \cdot 3HCl \cdot 3H_2O$ (FW = 567.16)

|   | Calcd. (%): | Found (%): |
|---|---|---|
| C | 44.47 | 44.53 |
| H | 9.60 | 9.66 |
| N | 7.41 | 7.36 |
| S | 11.31 | 11.41 |
| Cl | 18.75 | 18.75 |

EXAMPLE 8

Preparation and physical characteristics of technetium-99m-labeled Compound (11c)

ZF. Preparation of a non-radioactive carrier containing Compound (11c)

Under nitrogen stream, Compound (11c) (43 mg; 0.1 mmol) was dissolved in oxygen-free water (100 ml), followed by addition of anhydrous stannous chloride (9.48 mg; 50 μmol). The resultant solution was adjusted to pH 7.0 with 2N aqueous sodium hydroxide solution, filtered through a membrane filter of 0.22 μm (Millipore Co., Ltd.) for sterilization and dispensed each 1.0 ml into Ar-purged vials. The content in each vial contains Compound (11c) and can be used as a non-radioactive carrier for Tc-99m labeling (hereinafter referred to as "RI-11c").

ZG. Preparation of a radioactive diagnostic agent comprising technetium-99m-labeled Compound (11c)

To a vial containing BI-11c above prepared, sodium pertechnetate (technetium-99m) in saline (2.0 ml; 10 mCi) eluted from a generator (Mo-99 →Tc-99m) was added, and the resultant solution was heated at 100° C. for 10 minutes to give a radioactive diagnostic agent comprising technetium99m-labeled Compound (11c) (hereinafter referred to as "Tc-99m-(BI-11c)").

ZH. Thin layer chromatography for Tc-99m-(BI-11c)

An appropriate amount of Tc-99m-(BI-11c) was spotted onto a silica gel plate (silica gel 60, Merck Co., Ltd.) at a distance of 20 mm from the bottom and developed for 100 mm in a mixture of methylethylketone-methanol-ammonia water (10 : 9 : 1). After air-drying, the plate was scanned to determine the distribution of radioactivity with a thin layer radiochromatoscanner (Aloca Co.) and the radiochemical purity was calculated with a data processing apparatus (D-2000, by Hitachi Ltd.).

The obtained radioactivity peak was single (Rf: 0.68). This peak was attributed to the chelate compound (Tc-99m-(BI-11c)), because its Rf value was different from the Rf values for reduced $^{99m}TcO_2$ (Rf: 0) and pertechnetate ion (Rf: 0.98). Thus, the radiochemical purity of Tc-99m-(BI-11c) was assumed to be 100%.

ZI. Thin layer electrophoresis for Tc-99m-(BI-11c)

An appropriate amount of Tc-99m-(BI-11c) was spotted on an acetylated cellulose membrane and subjected to electrophoresis using 50 mM phosphate buffer (pH, 7.4) as an electrode buffer at a constant current of 0.5 mA/cm and at room temperature for 15 minutes. In the same manner as in ZH, the membrane was scanned to determine the distribution of radioactivity with a thin layer radioachromatoscanner. As the result, it was revealed that Tc-99m-(BI-11c) was a pure complex having a positive charge (reduced $^{99m}TcO_2$, non charge; $^{99m}TcO_4^-$, negative charge).

EXAMPLE 9

Preparation and physical characteristics of technetium-99m-labeled polyamine-dithiol compounds In the same manner as in Example 8 ZF, ZG, ZH and ZI but using other polyaminedithiol compounds instead of Compound (11c), preparation of non-radioactive carriers and radioactive diagnostic agents was made. The optimum labeling conditions for the polyaminedithiol compounds were studied. Furthermore, the physical characteristics of the produced technetium-99m-labeled polyaminedithiol compounds were evaluated. The results are shown in Table 16.

TABLE 16

| Polyaminedithiol compound | pH | Temperature at labeling (°C.) | TLC (Rf) | EP (Charge) | Radiochemical purity (%) |
|---|---|---|---|---|---|
| 11a | 7.0 | 100 | 0.10 | + | 100 |
| 11b | 7.0 | 100 | 0.81 | + | 100 |
| 11d | 7.0 | 100 | 0.91 | o | 100 |
| 11g | 6.0 | 100 | 0.78 | o | 98 |
| 11i | 7.1 | 25 | 0.88 | + | 97 |
| 11k | 7.3 | 120 | 0.94 | + | 98 |
| 11l | 6.0 | 100 | 0.91 | + | 99 |
| 11m | 6.0 | 100 | 0.85 | o | 100 |
| 11n | 5.5 | 100 | 0.92 | + | 99 |
| 11o | 6.1 | 120 | 0.98 | + | 98 |
| 14a | 8.0 | 100 | 0.00 | + | 100 |
| 14b | 9.0 | 120 | 0.34 | + | 100 |
| 14d· | 7.5 | 25 | 0.97 | + | 98 |
| 14p | 7.0 | 100 | 0.83 | + | 100 |
| 14q | 9.0 | 120 | 0.10 | + | 100 |
| 14r | 9.0 | 100 | 0.40 | o | 100 |
| 14s | 8.0 | 100 | 0.25 | o | 99 |
| 14t | 9.0 | 100 | 0.07 | + | 97 |
| 14u | 9.0 | 25 | 0.17 | + | 99 |
| 14x | 9.0 | 25 | 0.81 | + | 100 |
| 14y | 8.0 | 25 | 1.00 | + | 100 |
| 11h | 4.3 | 100 | 0.50 | + | 89 |
| 11p | 2.5 | 100 | 0.85 | o | 100 |
| 11r | 5.7 | 25 | 0.81 | + | 100 |
| 11w | 2.0 | 100 | 0.99 | o | 98 |
| 11x | 3.3 | 120 | 0.73 | o | 99 |
| 11zc | 2.8 | 100 | 0.90 | + | 100 |
| 33 | 7.4 | 25 | 0.89 | o | 97 |

EXAMPLE 10

Biodistribution of Tc-99m-(BI-11o) in rabbits

Japanese white rabbits (male) were anesthetized with a pentobarbital solution (2.5 mg/kg), and Tc-99m(BI-11o) (0.2 ml, 0.5 Ci) was administered via the carotid artery under a gamma camera (GCA-90B, Toshiba Co., Ltd.). Then, imaging of 112 frames (30 seconds/frame) was made in minutes. A region of interest was drawn around brain on images, and the time-activity curve of the brain was obtained. Based on this curve, the biological half life of Tc-99m-(BI-11o) in the brain was calculated to give 20 minutes (18%) for the first phase and 200 minutes (82%) for the second phase.

In the same manner as above, imaging was carried out with I-123-IMP [Holman et al, Seminar in Nuclear Medicine, Vol. 15, 357–376, 1985] known as a brain imaging agent and $^{99m}$Tc-labeled diethylenetriaminepentaacetic acid ($^{99m}$Tc-DTPA) [Coman et al., Seminar in Nuclear Medicine, Vol. 16, 63–73, 1986] known as not accumulating in normal cerebral parenchymal cells. As the results, the biological half life of I-123-IMP was 71 minutes (39%) for the first phase and 98 minutes (61%) for the second phase, and that of $^{99m}$Tc-DTPA was 2 minutes (75%) for the first phase and 18 minutes (25%) for the second phase. Accumulation in the cerebral parenchymal cells was observed in the case of I-123-IMP, while no accumulation was seen in the case of $^{99m}$Tc-DTPA. It was thus concluded that the above examination procedure was suitable for evaluation of the accumulation in the brain and the disappearance from the brain.

In comparison with I-123-IMP, Tc-99m-(BI-11o) showed a longer biological half-life in the second phase and might be considered to be retained in the brain over a longer period of time. In addition, Tc-99m is more suitable for the characteristics of a gamma camera than I-123-IMP. Accordingly, Tc-99m-(BI-11o) has potential for use in the diagnosis of regional cerebral blood flow.

EXAMPLE 11

Biodistribution of technetium 99m-labeled polyaminedithiol compounds in rabbits

In the same manner as in Example 10 using other technetium-99m-labeled polyaminedithiol compounds instead of Tc-99m-(BI-11o), their biodistribution in rabbits was examined, and their biological half-life in the brain was calculated. The results are shown in Table 17.

TABLE 17

| Carrier | Biological half-life in brain | |
|---|---|---|
| | First phase (rate) | Second phase (rate) |
| BI-11d | 18 min (32%) | 184 min (68%) |
| BI-11g | 5 min (23%) | 60 min (77%) |
| BI-11i | 8 min (50%) | 686 min (50%) |
| BI-11k | 4 min (39%) | 21 min (61%) |
| BI-11l | 11 min (34%) | 132 min (66%) |
| BI-11m | 3 min (24%) | 58 min (76%) |
| BI-11n | 17 min (42%) | 198 min (58%) |
| BI-11h | 1 min (44%) | 40 min (56%) |
| BI-11p | 3 min (18%) | 83 min (82%) |
| BI-11r | 3 min (28%) | 36 min (72%) |
| BI-11w | 13 min (60%) | 144 min (40%) |
| BI-11x | 10 min (46%) | 150 min (54%) |
| BI-11xc | 1 min (18%) | 66 min (82%) |
| BI-33 | 7 min (26%) | 148 min (74%) |

What is claimed is:

1. A polyaminodithiol compound of the formula:

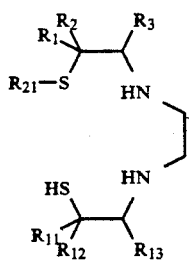

wherein $R_1$, $R_2$, $R_{11}$ and $R_{12}$ are each a lower alkyl group, $R_{21}$ is a hydrogen atom or a lower alkyl group, and $R_3$ and $R_{13}$ are each a hydrogen atom or a nitrogen-containing organic group, provided that at least one of $R_3$ and $R_{13}$ is a nitrogen-containing organic group, said nitrogen-containing organic group being a group of the formula: —A—N($R_4$)—$R_5$ wherein A is lower alkylene, and $R_4$ and $R_5$ are each a hydrogen atom, lower alkyl, cyclo(lower)alkyl or a group of the formula: —A'—N($R_6$)—$R_7$ (wherein A' is lower alkylene, and $R_6$ and $R_7$ are each a hydrogen atom, lower alkyl or cyclo(lower)alkyl, or $R_6$ and $R_7$ are combined together with the adjacent nitrogen atom to form a substituted or unsubstituted 5 to 8-membered nitrogen-containing saturated heterocyclic group), or $R_4$ and $R_5$ are combined together with the adjacent nitrogen atom to form a substituted or unsubstituted 5 to 8-membered nitrogen-containing saturated heterocyclic group.

2. The compound according to claim 1, wherein $R_1$, $R_2$, $R_{11}$ and $R_{12}$ are each methyl or ethyl.

3. The compound according to claim 1 or 2, wherein $R_{21}$ is ethyl or butyl.

4. The compound according to claim 1 or 2, wherein the nitrogen-containing organic group is amino(lower)alkyl, lower alkylamino(lower)alkyl, di(lower)alkylamino(lower)alkyl, piperidino(lower)alkyl, pierazino(lower)alkyl, pyrrolidino(lower)alkyl, 4-lower alkylpiperazino(lower)alkyl, 4-lower alkylpiperidino(lower)alkyl, 4-phenyl(lower)alkylpiperazino(lower)alkyl, 4-phenylpiperidino(lower)alkyl, morpholino(lower)alkyl, lower alkylamino(lower)alkylamino(lower)alkyl, di(lower)alkylamino(lower)alkylamino(lower)alkyl, piperidino(lower)alkylamino(lower)alkyl, piperazino(lower)alkylamino(lower)alkyl, 4-(lower)alkylpiperazino(lower)alkylamino(lower)alkyl, 4-phenyl(lower)alkylpiperazino(lower)alkylamino(lower)alkyl, lower cycloalkylamino(lower)alkyl or morpholino(lower)alkylamino(lower)alkyl.

5. The compound according to claim 1 or 2, wherein the nitrogen-containing organic group is aminomethyl, propylaminomethyl, isopropylaminomethyl, butylaminomethyl, isobutylaminomethyl, pentylaminomethyl, 1-methylbutylaminomethyl, hexylaminomethyl, N,N-diethylaminomethyl, N-butyl-N-ethylaminomethyl, N,N-dipropylaminomethyl, piperidinomethyl, piperazinomethyl, pyrrolidinomethyl, 4-methylpiperazinomethyl, 4-methylpiperidinomethyl, 4-benzylpiperazinomethyl, 4-phenylpiperidinomethyl, morpholinomethyl, N,N-dimethylaminoethylaminomethyl, N,N-diethylaminoethylaminomethyl, piperidinoethylaminomethyl, piperazinoethylaminomethyl, 4-methylpiperazinoethylaminomethyl, 4-isopropylpiperazinoethylaminomethyl, 4-benzylpiperazinoethylaminomethyl, 2-morpholinoethylaminomethyl, cycloehexylaminomethyl, or 3-morpholinopropylaminomethyl.

6. A chelate compound which comprises the compound according to claim 1 or 2 and a radioactive metal coordinated therewith.

7. The chelate compound according to claim 6, wherein the radioactive metal is technetium-99m.

8. A radioactive diagnostic compound which comprises the chelate compound according to claim 6 dissolved in a physiologically acceptable aqueous medium.

9. The compound according to claim 1 which is N-(2-mercapto-2-methylpropyl)-N'-[N,N-dipropylamino)-methyl-2-mercapto -2-methylpropyl]ethylenediamine.

10. The compound according to claim 1 which is N-(2-mercapto-2-methylpropyl)-N'-[2-mercapto-2-methyl-1-(4-methylpiperidino)methylpropyl]ethylenediamine.

* * * * *